(12) United States Patent
Sakakibara et al.

(10) Patent No.: US 10,267,877 B2
(45) Date of Patent: Apr. 23, 2019

(54) MAGNETIC FIELD HOMOGENEITY ADJUSTMENT METHOD, MAGNETIC FIELD HOMOGENEITY ADJUSTMENT PROGRAM AND MAGNETIC FIELD HOMOGENEITY ADJUSTMENT DEVICE

(71) Applicant: HITACHI, LTD., Tokyo (JP)

(72) Inventors: Kenji Sakakibara, Tokyo (JP); Takuya Fujikawa, Tokyo (JP); Mitsushi Abe, Tokyo (JP); Hikaru Hanada, Tokyo (JP)

(73) Assignee: HITACHI, LTD., Tokyo (JP)

( * ) Notice: Subject to any disclaimer, the term of this patent is extended or adjusted under 35 U.S.C. 154(b) by 0 days.

(21) Appl. No.: 15/542,493

(22) PCT Filed: Jan. 27, 2016

(86) PCT No.: PCT/JP2016/052259
§ 371 (c)(1),
(2) Date: Jul. 10, 2017

(87) PCT Pub. No.: WO2016/132832
PCT Pub. Date: Aug. 25, 2016

(65) Prior Publication Data
US 2018/0284205 A1    Oct. 4, 2018

(30) Foreign Application Priority Data
Feb. 20, 2015  (JP) ................... 2015-032339

(51) Int. Cl.
*G01R 33/3873*   (2006.01)
*A61B 5/055*   (2006.01)
(Continued)

(52) U.S. Cl.
CPC .......... *G01R 33/3873* (2013.01); *A61B 5/055* (2013.01); *G01R 33/243* (2013.01); *G01R 33/3815* (2013.01); *G01R 33/546* (2013.01)

(58) Field of Classification Search
CPC .................................................. G01R 33/3873
See application file for complete search history.

(56) References Cited

U.S. PATENT DOCUMENTS

2002/0043975 A1    4/2002   Aoki
2011/0057655 A1    3/2011   Ando et al.
(Continued)

FOREIGN PATENT DOCUMENTS

JP    2002-177243    6/2002
JP    2009-268791    11/2009
(Continued)

OTHER PUBLICATIONS

International Search Report dated Apr. 19, 2016 in connection with PCT/JP2016/052259.

*Primary Examiner* — Clayton E. LaBalle
*Assistant Examiner* — Jas A Sanghera
(74) *Attorney, Agent, or Firm* — Cooper & Dunham LLP

(57) ABSTRACT

Even if there is a restriction in an amount of magnetic pieces which can be disposed at each position in a shim tray, a distribution of a static magnetic field is measured so that an error magnetic field between the distribution of the static magnetic field and a target magnetic field is calculated, and respective reachable magnetic field homogeneities in a case where the magnetic pieces are disposed at one or more of the plurality of positions in the shim tray are calculated while changing the target magnetic field. The target magnetic field is selected in which an amount of magnetic pieces at each of the positions in the shim tray is equal to or less than a predetermined upper limit value, and the reachable magnetic (Continued)

field homogeneity is equal to or less than a predetermined value.

15 Claims, 15 Drawing Sheets

(51) Int. Cl.
*G01R 33/24* (2006.01)
*G01R 33/3815* (2006.01)
*G01R 33/54* (2006.01)

(56) References Cited

U.S. PATENT DOCUMENTS

| | | | |
|---|---|---|---|
| 2011/0089943 A1* | 4/2011 | Abe | G01R 33/3873 324/301 |
| 2012/0268119 A1 | 10/2012 | Abe et al. | |
| 2014/0009152 A1 | 1/2014 | Sakakibara | |

FOREIGN PATENT DOCUMENTS

| | | |
|---|---|---|
| JP | 2011-110065 | 6/2011 |
| JP | 2012-249765 | 12/2012 |
| WO | WO 2012/132911 A1 | 10/2012 |

* cited by examiner

FIG.1
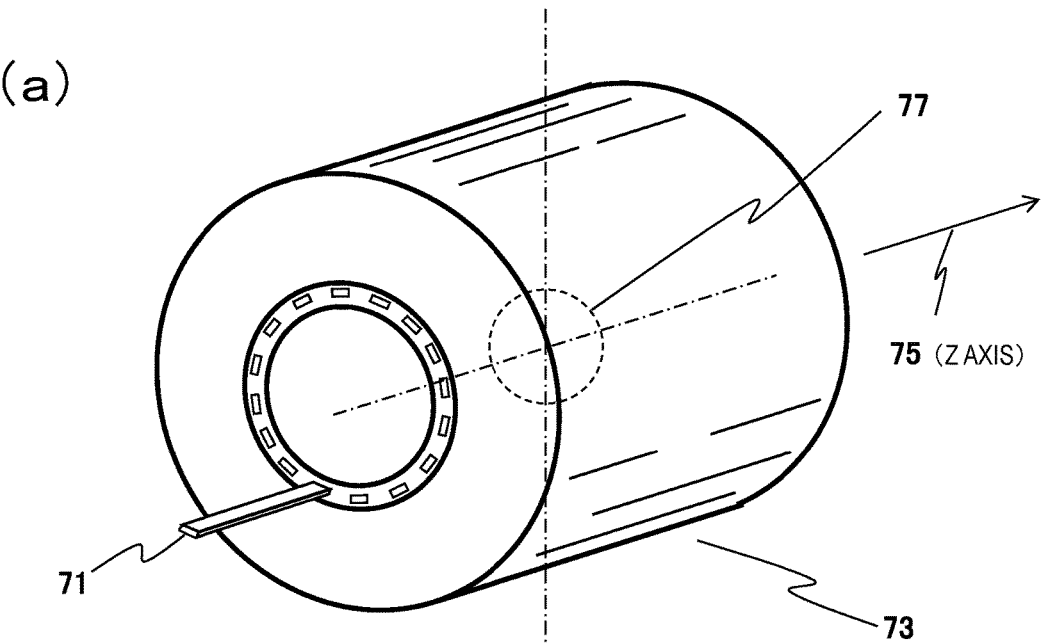
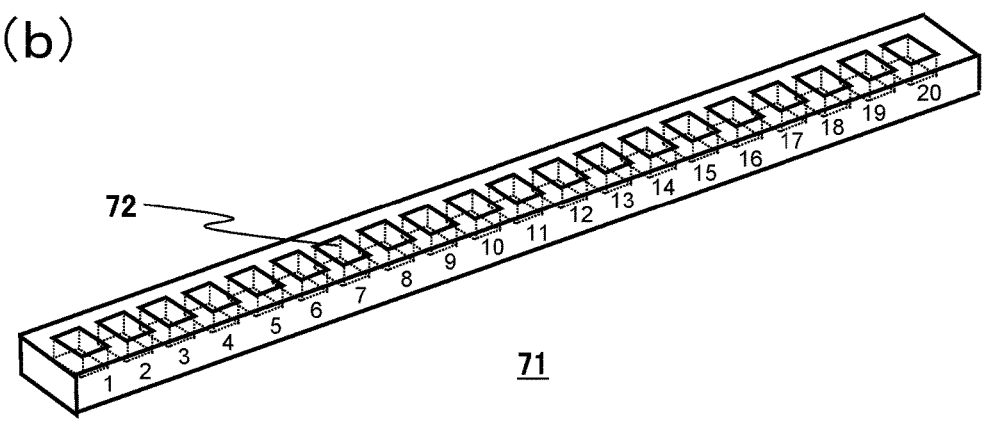

FIG.3
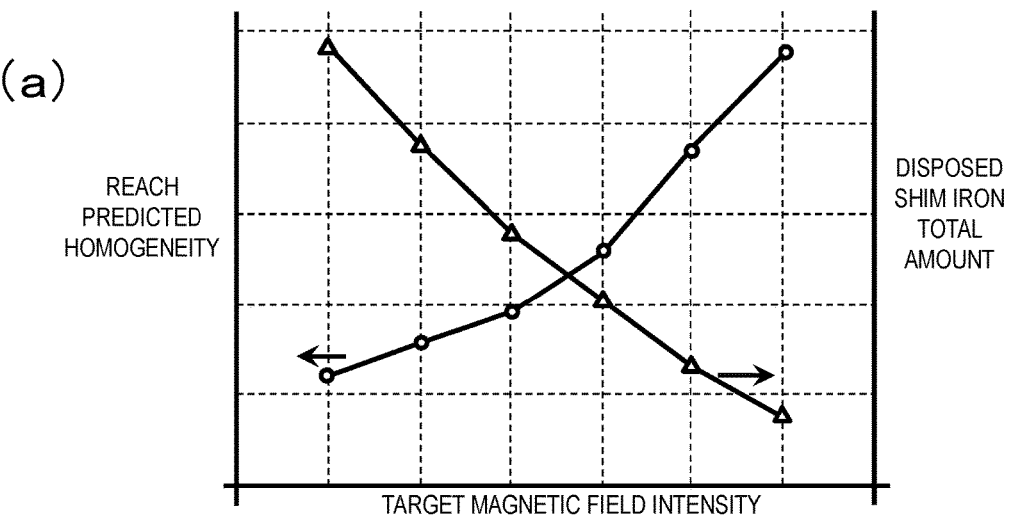
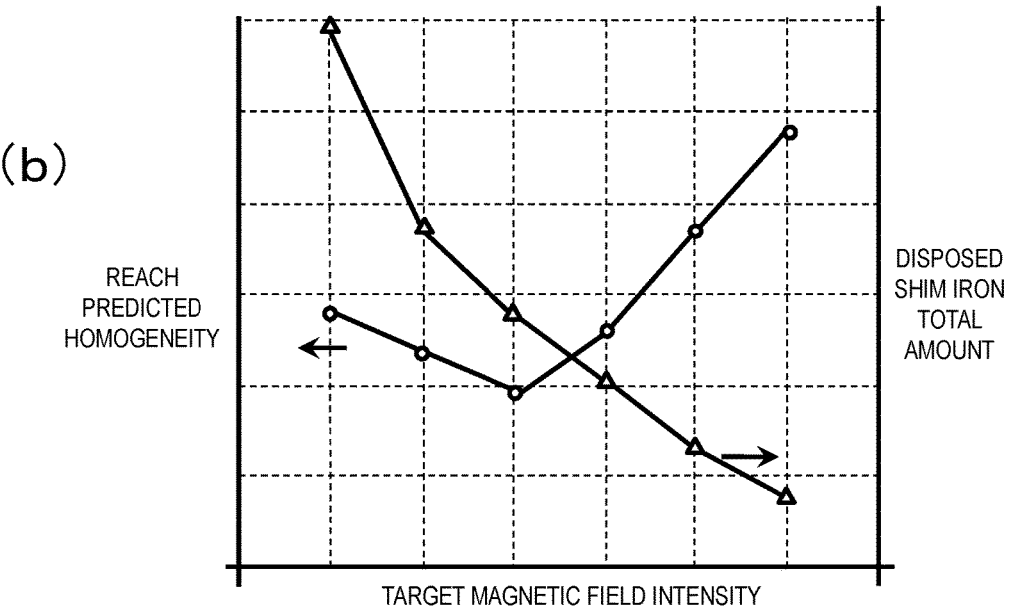

FIG.10

| SHIM IRON TO BE USED | LENGTH[mm] | WIDTH[mm]×LENGTH[mm] |
|---|---|---|
| A | 0.5 | 20×20 |
| B | 0.01 | 20×20 |

| TRAY NO. | NUMBER OF DEPRESSION 72 | | | | | | | | | | | | | | | | | | | | | |
|---|---|---|---|---|---|---|---|---|---|---|---|---|---|---|---|---|---|---|---|---|---|---|
| | 1 | | 2 | | 3 | | 4 | | 5 | | 6 | | ... | 20 | | 21 | | 22 | | 23 | | 24 | |
| | A | B | A | B | A | B | A | B | A | B | A | B | | A | B | A | B | A | B | A | B | A | B |
| 1 | 15 | 1 | | | | | | | | | | | | 2 | 5 | | | | | | | 1 | 5 |
| 2 | | | 1 | 1 | | | | | | | | | | | | | | | | | | | |
| 3 | 20 | | | | | | | | | | | | | 1 | | | 5 | | | | | 1 | 5 |
| 4 | 4 | 2 | | | | | | | | | | | | | | | | | | | | | |
| 5 | | | | | | | | | | | | | | | | | | | | | | | |
| 6 | | | | | | | 3 | 2 | 1 | 2 | | | | | 5 | | | | 1 | | | | 5 |
| 7 | 11 | 1 | | | | | | | | 5 | | | | | 3 | | | | | | | | 3 |
| 8 | | | | | | | | | 2 | 3 | | | | | | | | | | | | | |
| 9 | 5 | 1 | 1 | 1 | | | | | | | | | | | | | | | | | 2 | 5 | |
| 10 | | 3 | | | | | 3 | 2 | 1 | 2 | | | | | 5 | | 5 | | | | | 3 | 5 |
| 11 | 20 | | | | | | | | | | | | | 1 | | | | | 1 | | | 1 | |
| 12 | | | | | | | | | | | | | | | | | | | | | | | |

| PITCH WIDTH OF CENTER MAGNETIC FIELD | TARGET CENTER MAGNETIC FIELD INTENSITY $B_z$ [Tesla] | POSITIVE MAGNETIC FIELD MOMENT AMOUNT [m³] | NEGATIVE MAGNETIC FIELD MOMENT AMOUNT [m³] | REACH PREDICTED HOMOGENEITY [ppm] |
|---|---|---|---|---|
| $\Delta B = 5 \times 10^{-4}$ [Tesla] $n=6$ | 1.501348 | 1.2E-04 | -1.3E-03 | 10.2 |
| | 1.500848 | 2.7E-04 | -5.6E-04 | 9.3 |
| | 1.500348 | 7.8E-04 | -7.9E-05 | 9.7 |
| | 1.499848 | 1.3E-03 | 0.0E+00 | 9.9 |
| | 1.499348 | 2.2E-03 | 0.0E+00 | 12.1 |
| | 1.498848 | 3.1E-03 | -3.2E-06 | 14.8 |

(b)

| PITCH WIDTH OF CENTER MAGNETIC FIELD | TARGET CENTER MAGNETIC FIELD INTENSITY $B_z$ [Tesla] | POSITIVE MAGNETIC FIELD MOMENT AMOUNT [m³] | NEGATIVE MAGNETIC FIELD MOMENT AMOUNT [m³] | REACH PREDICTED HOMOGENEITY [ppm] |
|---|---|---|---|---|
| $\Delta B = 2 \times 10^{-4}$ [Tesla] $n=6$ | 1.500248 | 9.1W-04 | -3.0E-05 | 9.9 |
| | 1.500048 | 1.0E-03 | 0.0E+00 | 8.7 |
| | 1.499848 | 1.3E-03 | 0.0E+00 | 9.9 |
| | 1.499648 | 1.6E-03 | 0.0E+00 | 10.8 |
| | 1.499448 | 2.0E-03 | 0.0E+00 | 11.6 |
| | 1.499248 | 2.3E-03 | 0.0E+00 | 12.6 |

(c)

| PITCH WIDTH OF CENTER MAGNETIC FIELD | TARGET CENTER MAGNETIC FIELD INTENSITY $B_z$ [Tesla] | POSITIVE MAGNETIC FIELD MOMENT AMOUNT [m³] | NEGATIVE MAGNETIC FIELD MOMENT AMOUNT [m³] | REACH PREDICTED HOMOGENEITY [ppm] |
|---|---|---|---|---|
| $\Delta B = 1 \times 10^{-5}$ [Tesla] $n=6$ | 1.500068 | 9.8E-04 | -4.9E-10 | 8.5 |
| | 1.500058 | 9.9e-04 | 0.0E+00 | 8.6 |
| | 1.500048 | 1.0E-09 | 0.0E+00 | 8.7 |
| | 1.500038 | 1.0e-03 | 0.0E+00 | 8.8 |
| | 1.500028 | 1.0e-03 | 0.0E+00 | 8.9 |
| | 1.500018 | 1.0e-03 | 0.0E+00 | 9.0 |

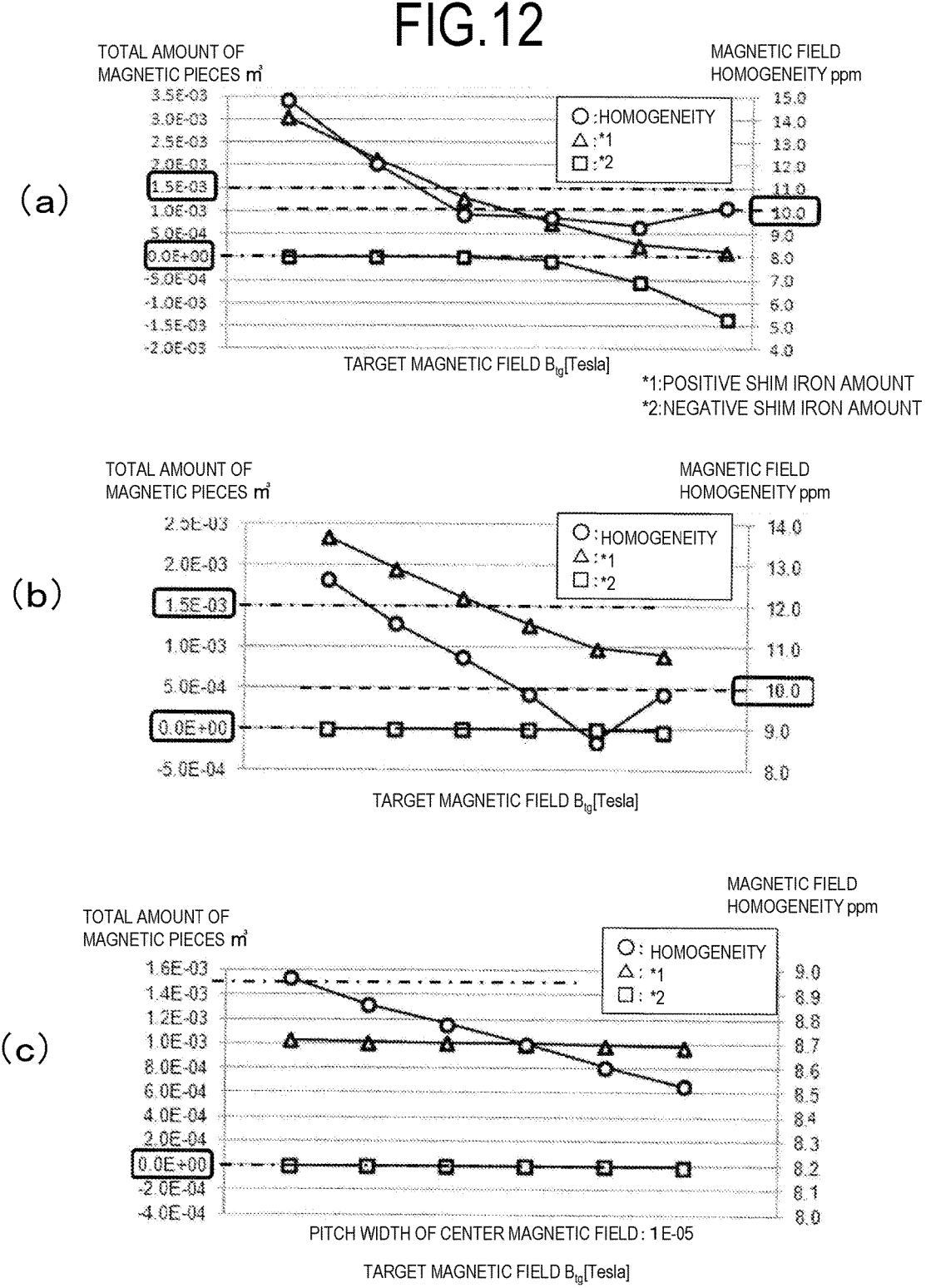

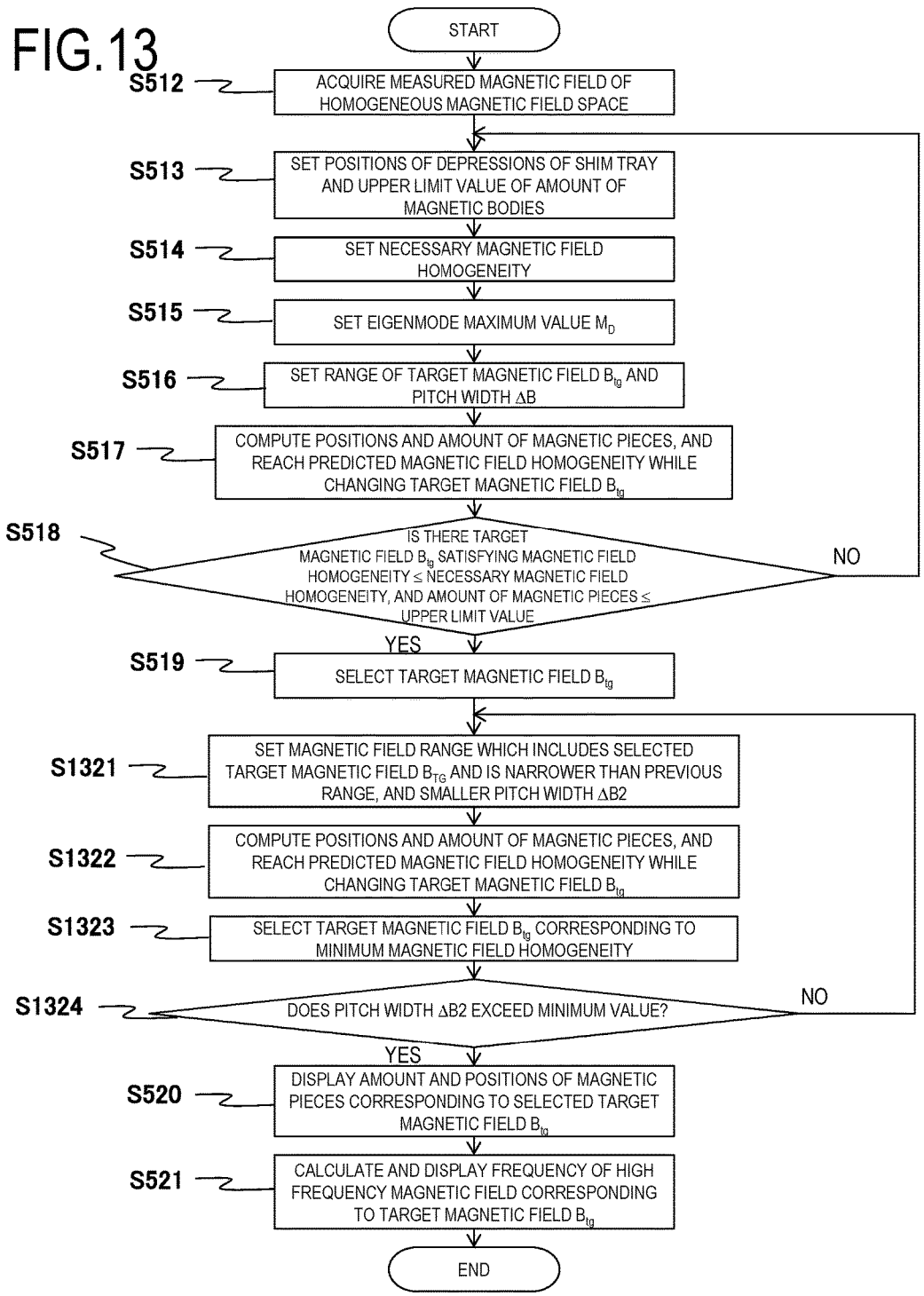

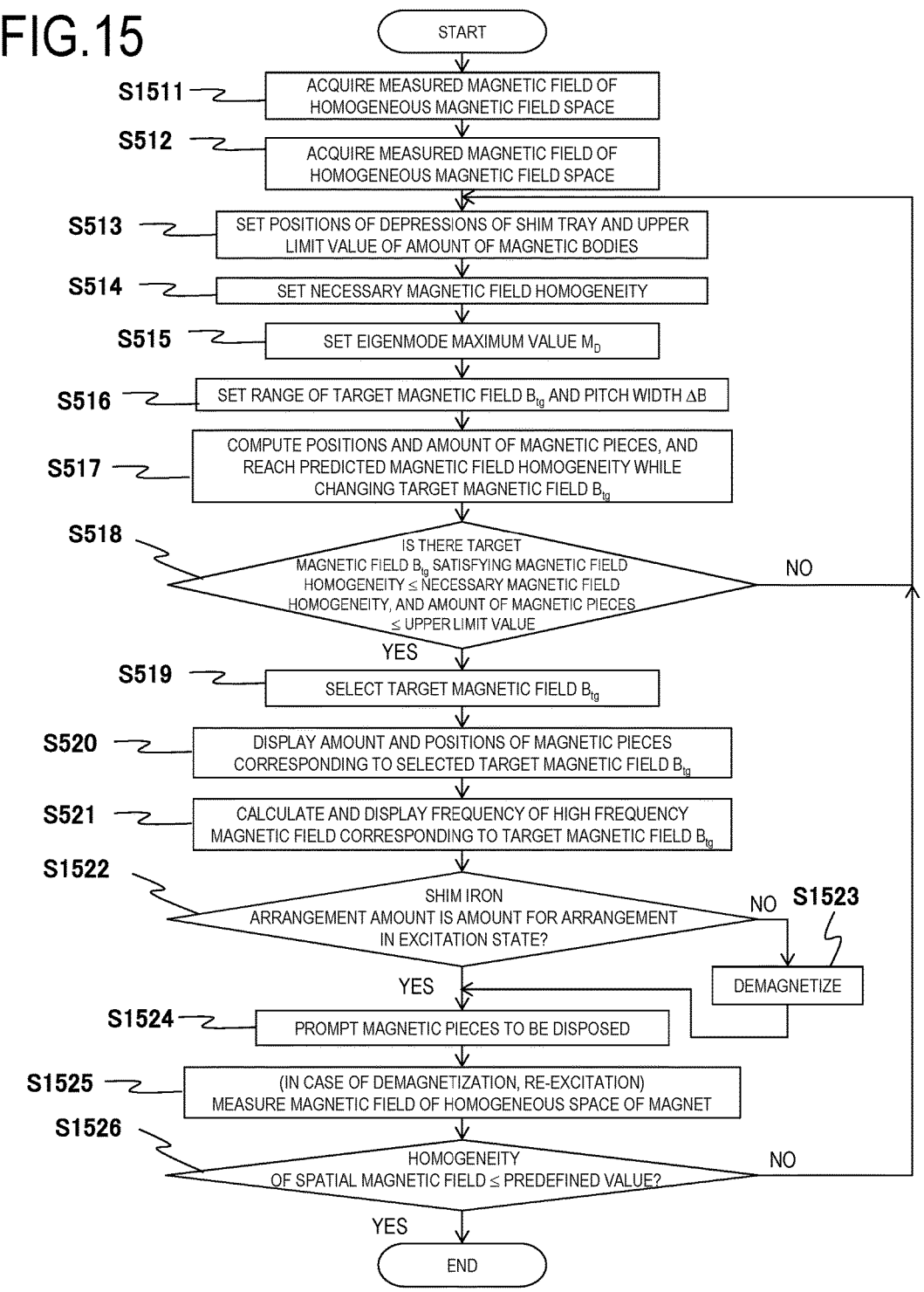

MAGNETIC FIELD HOMOGENEITY ADJUSTMENT METHOD, MAGNETIC FIELD HOMOGENEITY ADJUSTMENT PROGRAM AND MAGNETIC FIELD HOMOGENEITY ADJUSTMENT DEVICE

TECHNICAL FIELD

The present invention relates to a method and a program for adjusting magnetic field homogeneity of a static magnetic field generation device of magnetic resonance imaging (hereinafter, referred to as MRI), and a magnetic field homogeneity adjustment device.

BACKGROUND ART

An MRI apparatus measures magnetic resonance (hereinafter, referred to as NMR) signal of nucleus spins of an object disposed in an imaging space inside a homogeneous static magnetic field, and displays a nucleus spin density distribution, a relaxation time distribution, or the like of the object as a tomographic image. The MRI apparatus includes a static magnetic field generation device which generates a static magnetic field, and a gradient magnetic field generation device which generates a gradient magnetic field for adding position information to an NMR signal.

If disturbance occurs in the homogeneity of a static magnetic field generated by the static magnetic field generation device, the linearity of a gradient magnetic field superposed thereon deteriorates. Therefore, deviation occurs in position information added to an NMR signal, and this causes strain or a loss of an image. The strain or the loss of an image damages the accuracy or sharpness of the image and thus seriously impedes diagnosis. Therefore, extremely high homogeneity is required for a static magnetic field of an imaging space.

On the other hand, since the intensity of an NMR signal is substantially proportional to the intensity of a static magnetic field, a static magnetic field generation device which generates a static magnetic field with large intensity is desirable in order to obtain high quality MRI image. As mentioned above, high homogeneity and large magnetic field intensity (high magnetic field) are required for a static magnetic field generated by the MRI apparatus, and thus the static magnetic field generation device is one of considerably principal constituent elements of the MRI apparatus.

It is known that a static magnetic field generation device using a superconducting magnet stably forms a static magnetic field with high homogeneity and large intensity in an imaging space for a long period of time. It is known that a cylindrical superconducting magnet has a shape for generating a high magnetic field with high efficiency. The cylindrical superconducting magnet has a structure in which a plurality of superconducting coils are disposed in a cryostat, or a low-temperature container in which liquid helium or other low-temperature freezing media are enclosed.

The cryostat or the low-temperature container is disposed in a vacuum vessel, and a radiation shield for blocking permeation of heat from the outside is disposed inside the vacuum vessel. A freezer is attached to the vacuum vessel, and a cooling portion of the freezer is connected to the cryostat or the low-temperature container and the radiation shield so as to maintain a low temperature.

In an MRI apparatus in which a superconducting magnet is used for a static magnetic field generation device, a volume and a shape of an imaging space known as a field of view (FOV) differs depending on a necessary imaging target, but are defined by a peak-to-peak value of the magnetic field homogeneity, and the space has substantially a spherical shape. Recently, in an MRI apparatus in which the central magnetic field intensity is 1.5 teslas, a peak-to-peak value of the homogeneity of a static magnetic field has been generally several tens of ppm (about 20 to 40 ppm) at an FOV with a diameter of about 45 to 50 cm.

The homogeneity of a static magnetic field in a superconducting magnet is mainly defined by arrangement of superconducting coils, and thus the arrangement is designed so that a necessary homogeneous magnetic field is generated in a desired space. However, actually, it is hard to realize magnetic field homogeneity as designed due to a manufacturing dimension error of a superconducting magnet, and the homogeneity of a static magnetic field in a single superconducting magnet is about several hundreds of ppm at an FOV with a diameter of about 45 to 50 cm. Thus, in order to correct non-homogeneity of a static magnetic field in the superconducting magnet, a method is generally used in which minute magnetic pieces called a passive shim are disposed around an imaging space, and the static magnetic field is finely adjusted.

PTL 1 proposes a method in which an amount and positions of magnetic pieces to be disposed to adjust a magnetic field in a static magnetic field generation device are obtained through computation. In the adjustment method disclosed in PTL 1, a spatial distribution of a magnetic field in an imaging space is measured, and an amount and arrangement of magnetic pieces for correcting an error magnetic field with respect to a desired homogeneous magnetic field are calculated by using an eigen distribution function obtained through singular value decomposition.

CITATION LIST

Patent Literature

PTL 1: Japanese Patent No. 4902787

SUMMARY OF INVENTION

Technical Problem

A static magnetic field generation device of an MRI apparatus is required to realize correction of a static magnetic field by using shim iron pieces while securing a large imaging space into which an object is inserted. Thus, a shim tray in which a plurality of depressions in each of which a plurality of shim iron pieces can be disposed are provided to be arranged is provided on the imaging space side of the static magnetic field generation device. A size (depth) of the depression of the shim tray has a restriction in order to secure a size of the imaging space, and an amount of magnetic pieces which can be disposed in a single depression has an upper limit. It is necessary to realize a static magnetic field with desired homogeneity or higher by using magnetic pieces of an upper limit value or less.

The disposed shim iron pieces generate not only a magnetic field component for correcting an error magnetic field but also a homogeneous static magnetic field component (B0 component) An amount of the generated B0 component at this time tends to be substantially proportional to a total amount of shim iron. On the other hand, magnetization of the shim iron pieces is influenced by the room temperature or a temperature due to heat generated by a gradient magnetic field coil disposed near a static magnetic field space, and, as a result, a static magnetic field varies. Particularly, the B0 component is most sensitive to a temperature, and thus it is necessary to set a certain extent of restriction for a total amount of shim iron pieces separately from the above-described arrangement amount for each depression.

PTL 1 discloses that, if a target magnetic field is changed, the intensity of each eigen distribution included in an error magnetic field and magnetic field intensity (reach homogeneity) remaining as a residual are also changed, and thus it is necessary to take into consideration the target magnetic field when selecting an eigen distribution (paragraphs 0051 and 0069). However, a case where there is an upper limit in an amount of magnetic pieces which can be disposed is not taken into consideration in the technique disclosed in PTL 1, and thus a relationship between an upper limit in an amount of magnetic pieces and a target magnetic field or reach homogeneity is not disclosed.

An object of the invention is to achieve high magnetic field homogeneity even if there is a restriction in an amount of magnetic pieces which can be disposed at each position in a shim tray.

Solution to Problem

In order to achieve the above-described object, according to the invention, there is provided a magnetic field homogeneity adjustment method using singular value decomposition for a static magnetic field generation device including a shim tray for holding magnetic pieces for adjusting the homogeneity of a generated static magnetic field at a plurality of predetermined positions.

In other words, the method includes measuring a distribution of a static magnetic field generated by the static magnetic field generation device so as to calculate an error magnetic field between the distribution of the static magnetic field and a target magnetic field; calculating respective reachable magnetic field homogeneities in a case where the magnetic pieces are disposed at one or more of the plurality of positions in the shim tray while changing the target magnetic field within a predetermined magnetic field range; and selecting the target magnetic field in which an amount of magnetic pieces at each of the positions in the shim tray is equal to or less than a predetermined upper limit value, and the reachable magnetic field homogeneity is equal to or less than a predetermined value, and disposing the magnetic pieces of the amount corresponding to the target magnetic field in the shim tray.

Advantageous Effects of Invention

According to the invention, it is possible to perform efficient adjustment to high magnetic field homogeneity even if there is an upper limit value in an amount of magnetic pieces which can be disposed at each position in a shim tray.

BRIEF DESCRIPTION OF DRAWINGS

FIG. 1(a) is a perspective view illustrating an example of a static magnetic field generation device (a state in which a shim tray 71 is partially extracted), and FIG. 1(b) is a perspective view of the shim tray 71.

FIG. 3(a) is a graph illustrating a relationship among a target magnetic field intensity, reachable magnetic field homogeneity, and a total amount of necessary magnetic shims, and FIG. 3(b)) is a graph illustrating a relationship among a target magnetic field intensity, reachable magnetic field homogeneity, and a total amount of magnetic shims in a case where there is an upper limit in a capacity of depressions of the shim tray.

FIG. 10 is a table illustrating a relationship among a shim tray displayed in S520 in FIG. 5, a number of a depression 72, and a magnetic body amount.

FIGS. 11(a) to 11(c) are tables illustrating calculation results in S517 in FIG. 5.

FIGS. 12(a) to 12(c) are tables illustrating calculation results in FIGS. 11(a) to 11(c).

FIG. 13 is a flowchart illustrating an operation of a magnetic field homogeneity adjustment program according to a second embodiment.

FIG. 15 is a flowchart illustrating an operation of a magnetic field homogeneity adjustment program according to the third embodiment.

DESCRIPTION OF EMBODIMENTS

Figure 2:
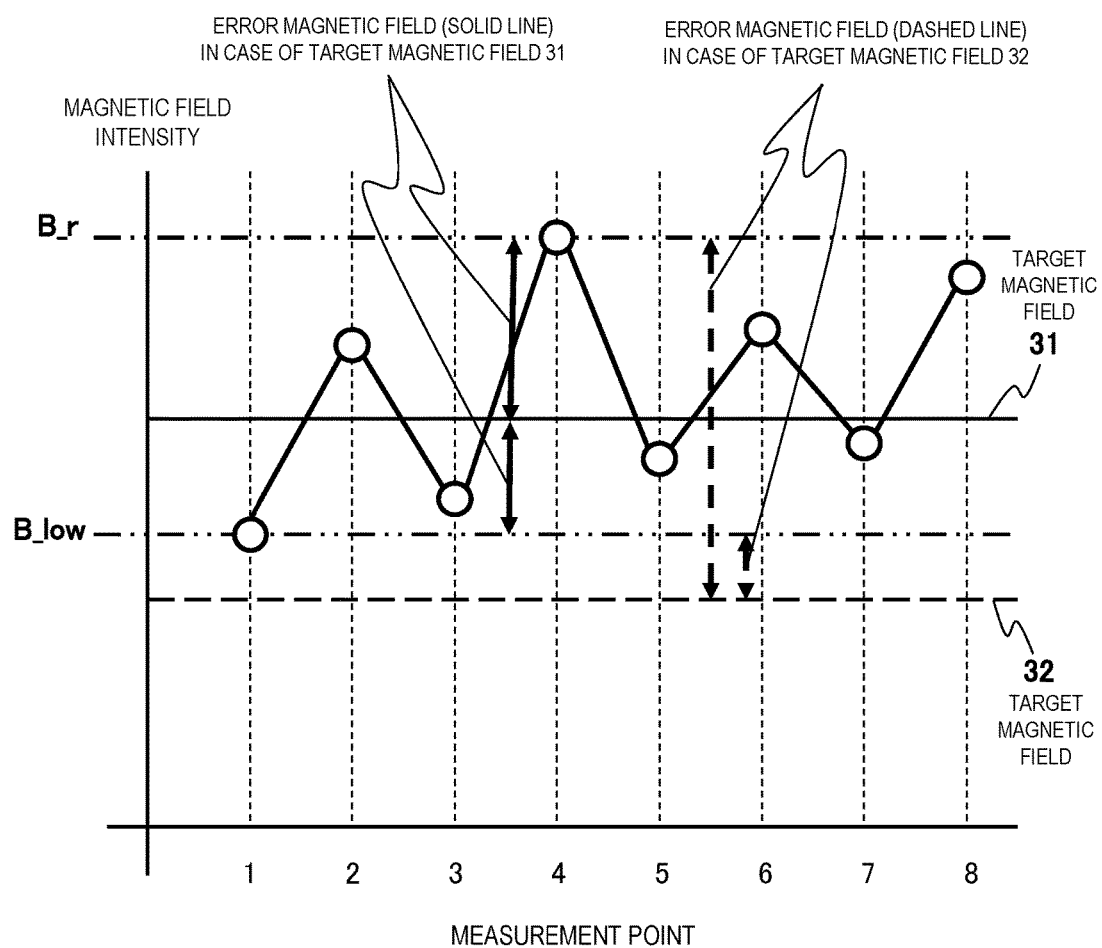
FIG. 2 is a graph illustrating an example of a distribution of measured magnetic field intensities.

Embodiments of the invention will be described with reference to the drawings.

<<First Embodiment>>

A description will be made of a static magnetic field adjustment method according to a first embodiment of the invention. The static magnetic field adjustment method of the present embodiment is a method of adjusting magnetic field homogeneity of a static magnetic field generation device 73 including a shim tray 71 as illustrated in FIG. 1. The shim tray 71 includes depressions 72 at a plurality of predetermined positions (numbers 1 to 20) so that magnetic pieces for the static magnetic field generation device 73 adjusting the homogeneity of a static magnetic field generated in a homogeneous magnetic field space 77 are held at the positions (numbers 1 to 20). A plurality of shim trays 71 are disposed to be arranged on the homogeneous magnetic field space 77 side of the static magnetic field generation device 73.

Consequently, a plurality of positions 1 to 20 for disposing the magnetic pieces of the plurality of shim trays 71 are disposed in a matrix.

In the present embodiment, a case where the static magnetic field generation device 73 is a static magnetic field generation device of an MRI apparatus is described as an example, but the method of the present embodiment is applicable to static magnetic field adjustment of other apparatuses requiring a homogeneous static magnetic field without being limited to the MRI apparatus. FIG. 1 illustrates an example in which the cylindrical static magnetic field generation device is disposed so that a static magnetic field direction (Z axis) is a horizontal direction, but the invention is applicable to a static magnetic field generation device in which a pair of tabular magnets are disposed vertically with a gap and a static magnetic field direction is a vertical direction. Hereinafter, a case where the static magnetic field generation device uses a superconducting magnet will be described, but the static magnetic field generation device may use a normal conducting magnet or a permanent magnet.

In the magnetic field homogeneity adjustment method of the present embodiment, in order for the magnetic field homogeneity of the homogeneous magnetic field space 77 to be equal to or less than a predetermined value, positions and an amount of magnetic pieces to be disposed in the depressions 72 at the positions (numbers 1 to 20) of the plurality of shim trays 71 are obtained through computation using singular value decomposition. In this case, a size (depth) of each of the depressions 72 of the shim tray 71 is defined in advance in order to secure the large homogeneous magnetic field space 77.

Thus, an amount (capacity) of magnetic pieces which can be disposed in the depressions 72 at the positions (numbers 1 to 20) has an upper limit. The present inventor or the like has found that, in a case where there is an upper limit in an amount of magnetic pieces which can be disposed, the reachable minimum magnetic field homogeneity is changed by changing a target magnetic field. Therefore, the homogeneous magnetic field space 77 in which the magnetic field homogeneity is smaller (a distribution of a magnetic field is smaller) is formed by changing a target magnetic field within an allowable range. Regarding a method of computing arrangement and an amount of magnetic pieces by using the singular value decomposition, a well-known method is used (for example, Japanese Patent No. 4902787).

A description will be made of a principle in which the reachable minimum magnetic field homogeneity is changed by changing a target magnetic field. Assuming that magnetic field intensities measured at a plurality of measurement points in the homogeneous magnetic field space 77 are distributed, for example, as illustrated in FIG. 2, magnetic pieces are required to be disposed in the shim tray 71 so that a magnetic field for correcting an error magnetic field between a target magnetic field 31 and the measured magnetic field intensity is generated.

In a case where iron pieces are disposed as magnetic pieces in the shim tray 71, the iron pieces are magnetized in the same orientation as that of a magnetic field of the homogeneous magnetic field space 77 by a magnetic field generated by the static magnetic field generation device 73, so as to have magnetic moment (hereinafter, referred to as positive magnetic moment), and thus generate a magnetic field. In a case where iron pieces having the positive magnetic moment are disposed near the homogeneous magnetic field space 77, magnetic flux of the magnetic field generated by the iron pieces passes through the homogeneous magnetic field space 77 in an opposite orientation to the orientation of the magnetic field of the homogeneous magnetic field space 77, and this reduces the magnetic field of the homogeneous magnetic field space 77.

Consequently, in the magnetic field intensity distribution in FIG. 2, the error magnetic field higher than the target magnetic field 31 can be lowered toward the target magnetic field 31. On the other hand, in order to heighten a magnetic field lower than the target magnetic field 31 toward the target magnetic field 31, a method is used in which iron pieces are disposed in the depressions 72 at positions separated from the homogeneous magnetic field space 77 in an axial direction so that, when magnetic flux of the magnetic field generated by the iron pieces having the positive magnetic moment passes through the homogeneous magnetic field space 77, the magnetic flux has the same orientation as the orientation of the magnetic field of the homogeneous magnetic field space 77.

Alternatively, permanent magnet pieces which is magnetized in an opposite orientation to the orientation of the homogeneous magnetic field space 77, that is, has negative magnetic moment may be disposed as magnetic pieces in the depressions 72 around the homogeneous magnetic field space 77, and thus adjustment may be performed by generating a magnetic field in the same orientation as the orientation of the static magnetic field in the homogeneous magnetic field space 77.

As mentioned above, positions and an amount of magnetic pieces for reducing the magnetic field intensity of the homogeneous magnetic field space 77 and magnetic pieces for increasing the magnetic field intensity are changed depending on what magnetic field intensity the target magnetic field 31 is set to.

FIG. 3(a) illustrates the target magnetic field 31, a predicted value (reach predicted homogeneity: left longitudinal axis) of the magnetic field homogeneity of the homogeneous magnetic field space 77, and a total amount of disposed magnetic pieces (disposed shim iron total amount: right longitudinal axis).

For example, as illustrated in FIG. 3(a), as a target magnetic field is reduced, more magnetic pieces are necessary, but the magnetic field of the homogeneous magnetic field space 77 can be made to gradually approach the target magnetic field. Particularly, in a case where a target magnetic field 32 lower than a lower limit of the magnetic field intensity distribution of the homogeneous magnetic field space 77 is set, it is not necessary to increase the magnetic field intensity distribution to the target magnetic field, and the magnetic field of the homogeneous magnetic field space 77 can be made to gradually approach the target magnetic field 32 by disposing many magnetic pieces for reducing the magnetic field intensity of the homogeneous magnetic field space 77.

However, since the capacity of the depression 72 of the shim tray 71 has an upper limit value, in a case where an amount of magnetic pieces which are required to be disposed exceeds the upper limit value, an error magnetic field cannot be corrected, and cannot be made to be gradually approach the target magnetic field 32. Here, FIG. 3(b) illustrates a relationship between an amount of magnetic pieces and the magnetic field homogeneity of the homogeneous magnetic field space 77 in a case where there is an upper limit in the capacity of the depression 72 of the shim tray 71. As described above, if a target magnetic field is set to be low, an amount of magnetic pieces is increased in order to correct an error magnetic field, and the magnetic field homogeneity tends to decrease (improve). However, since there is an upper limit in the capacity of the depression 72, all of necessary magnetic pieces cannot be disposed at a location which is required to correct an error magnetic field, and thus the magnetic field homogeneity has an extreme value.

As mentioned above, in a case where an amount of magnetic pieces to be disposed at any position, obtained through the computation, is more than the upper limit value of the capacity of the depression 72 of the shim tray 71, the magnetic pieces of the amount cannot be actually disposed in the shim tray 71. Thus, an error magnetic field cannot be corrected, and matching with a target magnetic field cannot be performed. Therefore, in a case where there is an upper limit value in an amount of magnetic pieces which can be disposed at the respective positions (numbers 1 to 20) of the shim tray 71, the reachable minimum magnetic field homogeneity differs depending on a value of the target magnetic field 31.

Since it is not easy to finely process a permanent magnet to a minute size, it is desirable to adjust the magnetic field homogeneity without using a permanent magnet having negative magnetic moment as a magnetic piece if at all possible.

Therefore, in the present embodiment, reachable magnetic field homogeneity is calculated by changing a target magnetic field within a predetermined range, and thus a target magnetic field for achieving predetermined magnetic field homogeneity or less is selected by using an amount of magnetic pieces which is equal to or less than an upper limit value. Hereinafter, details thereof will be described.

Figure 4:
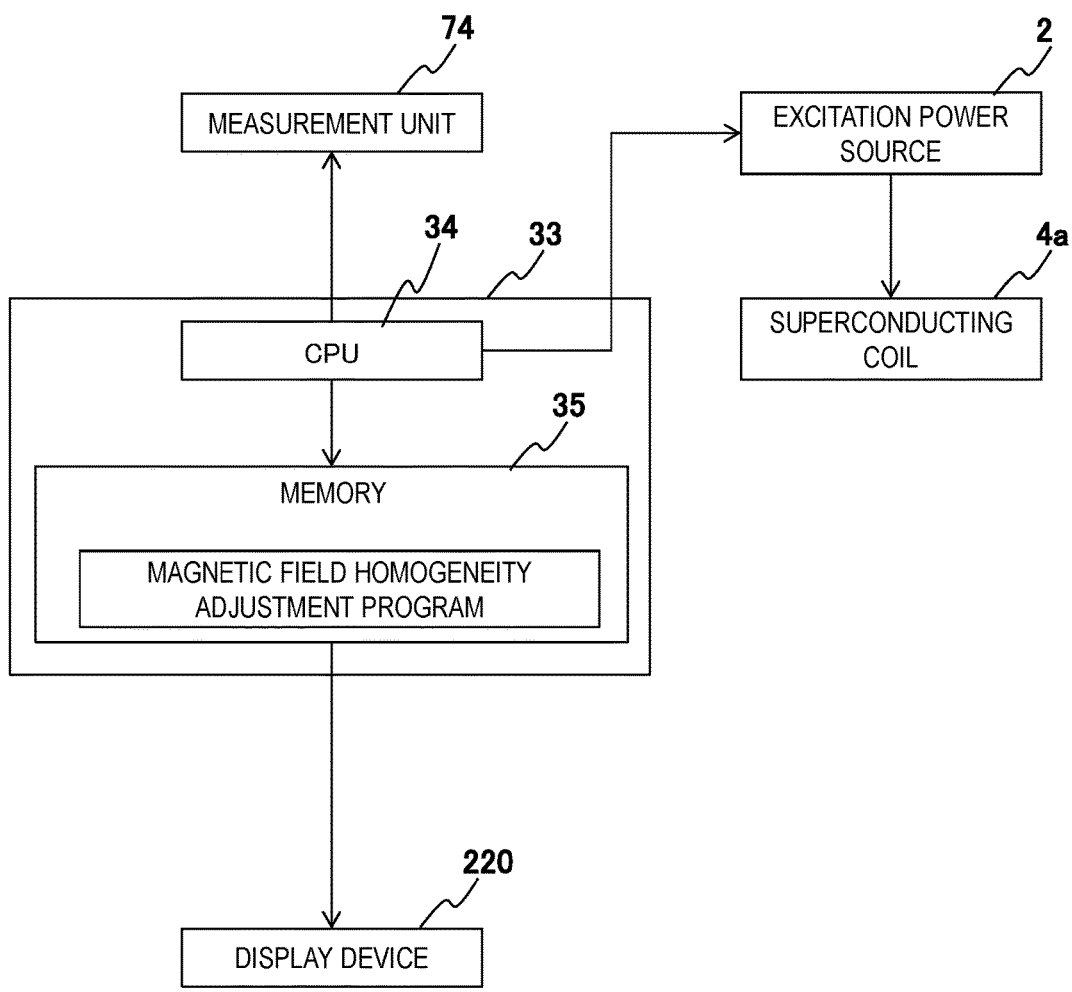
FIG. 4 is a block diagram illustrating a configuration of a magnetic field homogeneity adjustment device according to a first embodiment.

In the present embodiment, as illustrated in FIG. 4, a homogeneous magnetic field adjustment device 33 including a CPU 34 and a memory 35 is used. The memory 35 stores a predefined magnetic field homogeneity adjustment program, the CPU 34 reads the program in the memory 35 and executes the program, so as to operate as in a flow illustrated in FIG. 5, and thus realizes a magnetic field homogeneity adjustment method of the present embodiment. FIG. 4 illustrates an example in which the homogeneous magnetic field adjustment device 33 is connected to a measurement unit 74 and an excitation power source 2 of a superconducting coil 4*a*, but may not be connected thereto in the first embodiment.

Figure 6:
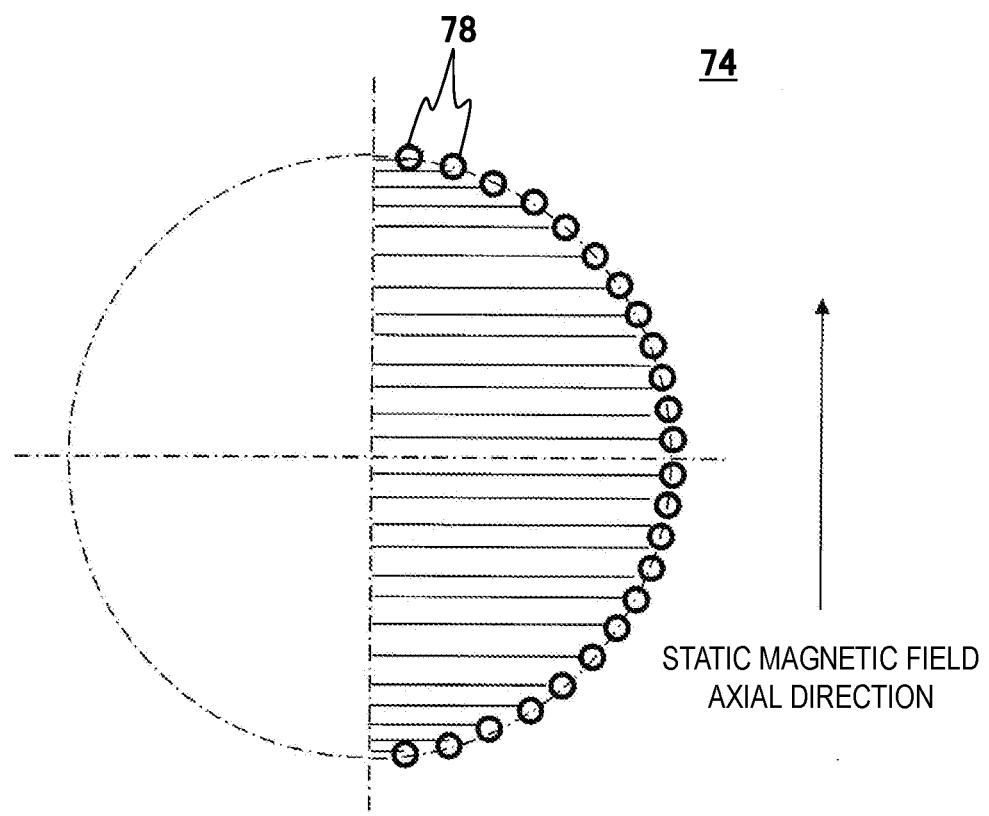
FIG. 6 is an explanatory diagram illustrating a configuration of a magnetic field measurement unit 74.

First, an operator measures a distribution of magnetic field intensities of the homogeneous magnetic field space 77. For example, as illustrated in FIG. 6, the measurement unit 74 in which magnetic field measurement elements 78 are disposed to be arranged in a predetermined pattern (for example, 24 planes) corresponding to a shape of the homogeneous magnetic field space 6 is rotated centering on an axial direction 75 of the static magnetic field, and thus magnetic field intensity $B_m$ of the homogeneous magnetic field space 77 is measured.

Figure 5:
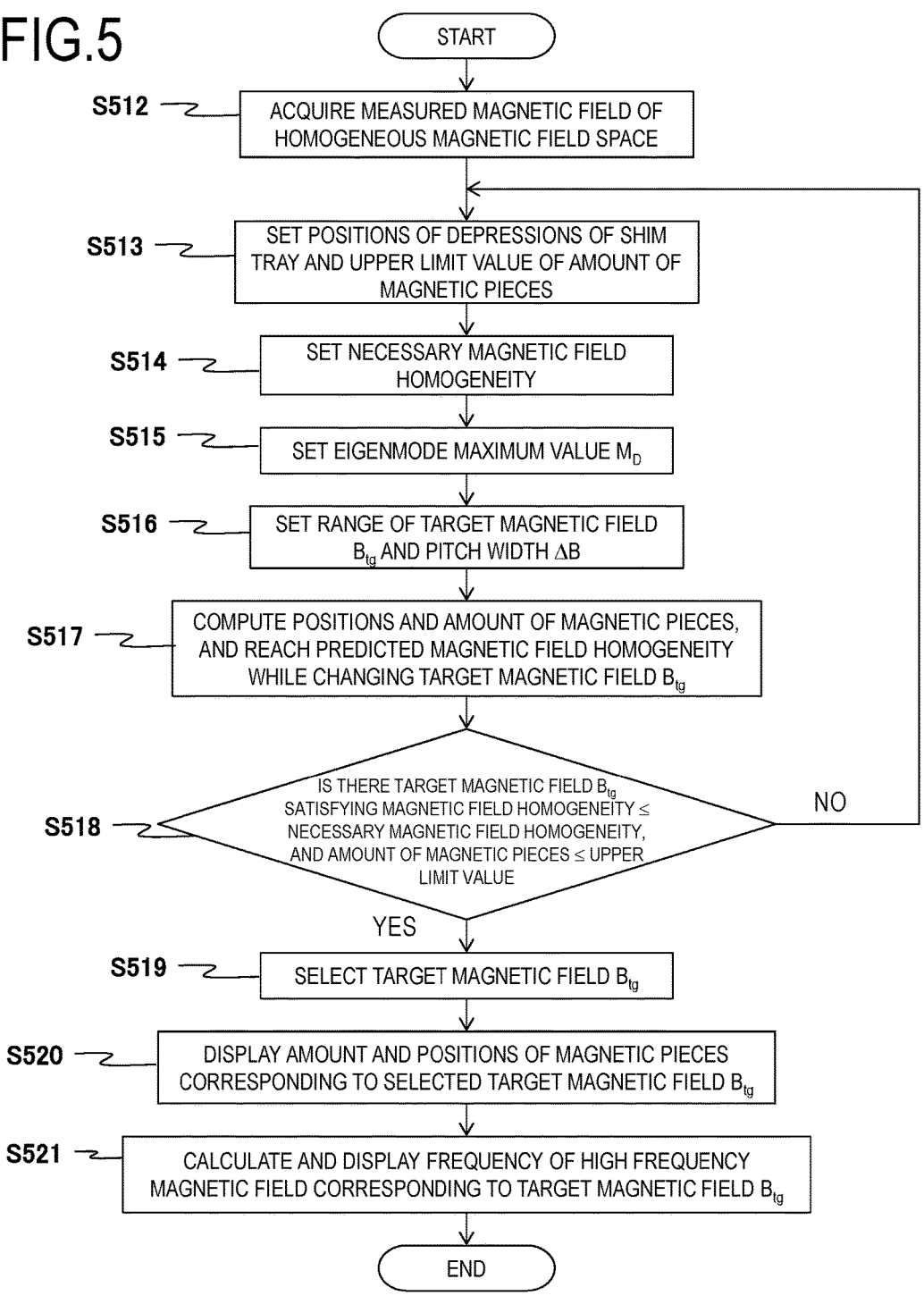
FIG. 5 is a flowchart illustrating an operation of a magnetic field homogeneity adjustment program according to the first embodiment.

The CPU 34 acquires the magnetic field intensity $B_m$ which is a measurement result in S512 in FIG. 5.

In S513 to S516, the CPU 34 receives position information of the depressions 72 at the positions (numbers 1 to 20) of the plurality of shim trays 71, an upper limit value of an amount of magnetic pieces (shim iron amount) which is permitted to be disposed in each depression 72, an upper limit value of a total capacity of magnetic pieces disposed in all of the depressions 72 of the shim tray 71, necessary magnetic field homogeneity, a range of a target magnetic field $B_{tg}$, and the maximum value of a eigenmode used for computation.

Figure 7:
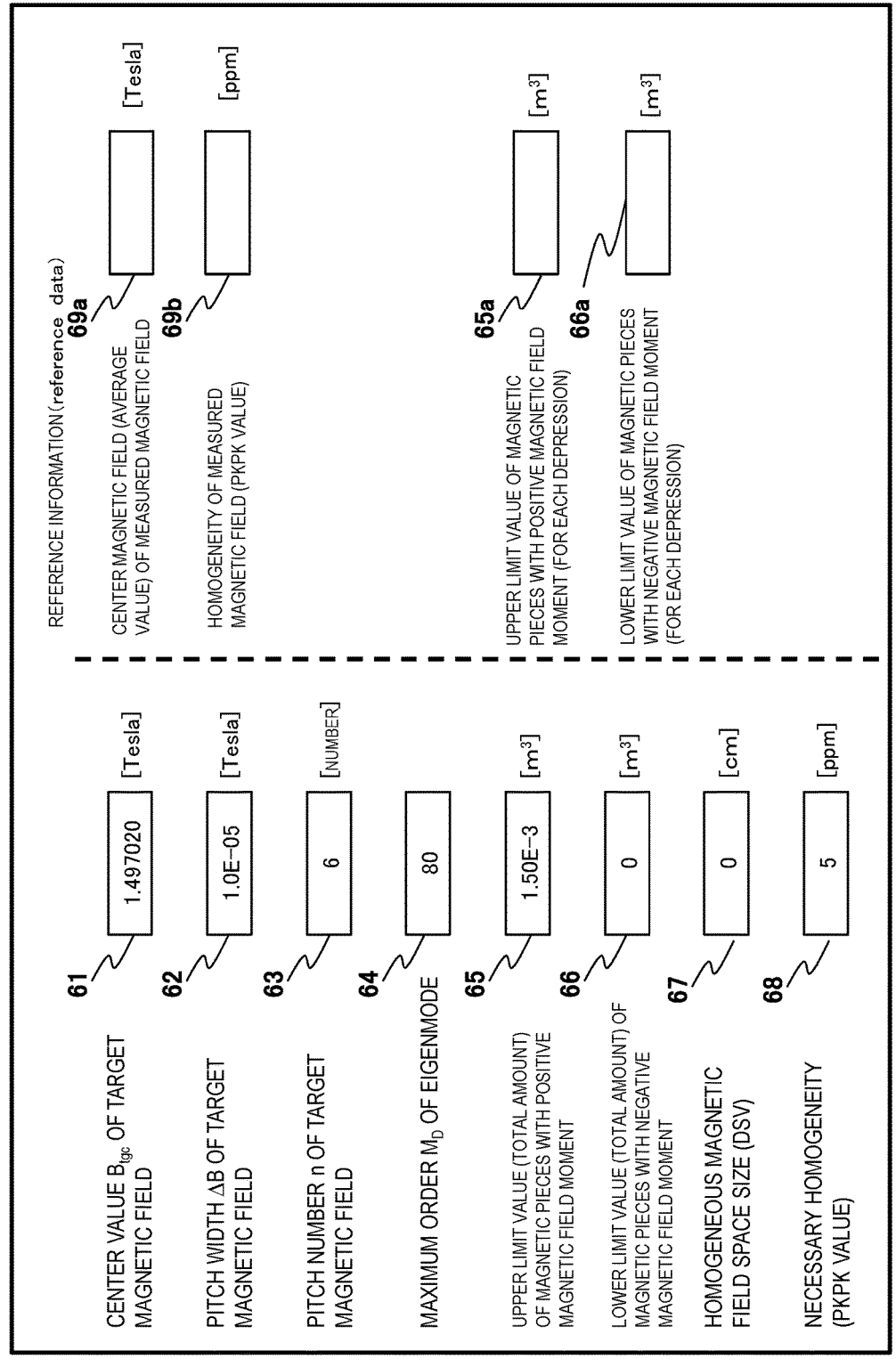
FIG. 7 is an explanatory diagram illustrating a screen for receiving setting of conditions from an operator in the first embodiment.

For example, the CPU 34 may display a reception screen as illustrated in FIG. 7 on a display device 220 connected thereto, and may receive a center value (target center magnetic field $B_{tgc}$) of the target magnetic field $B_{tg}$, a pitch width $\Delta B$ thereof, and a pitch number n (where n is an integer) which are input from the operator in input columns 61 to 63 of the reception screen. In this case, a range of the target magnetic field $B_{tg}$ is indicated by ($B_{tgc} - \Delta B \cdot n/2$) to ($B_{tgc} + \Delta B \cdot n/2$).

The maximum value of an eigenmode used for computation may be received in an input column 64; an upper limit value of a total amount of magnetic pieces (positive magnetic moment) permitted to be disposed in the entire shim tray 71 may be received in an input column 65; a lower limit value of a total amount of magnetic pieces (negative magnetic moment) permitted to be disposed may be received in the entire shim tray 71 in an input column 66; an upper limit value of an amount of magnetic pieces (positive magnetic moment) permitted to be disposed may be received in a single depression 72 in an input column 65*a*; an upper limit value of an amount of magnetic pieces (negative magnetic moment) permitted to be disposed in a single depression 72 may be received in an input column 66*a*; and necessary magnetic field homogeneity may be received in an input column 68.

Next, in S517, the CPU 34 calculates the minimum magnetic field homogeneity which can be reached in a case where magnetic pieces are disposed at one or more of the positions (numbers 1 to 20) of the plurality of shim trays 71, while changing the target magnetic field $B_{tg}$ within the received magnetic field range.

Figure 8:
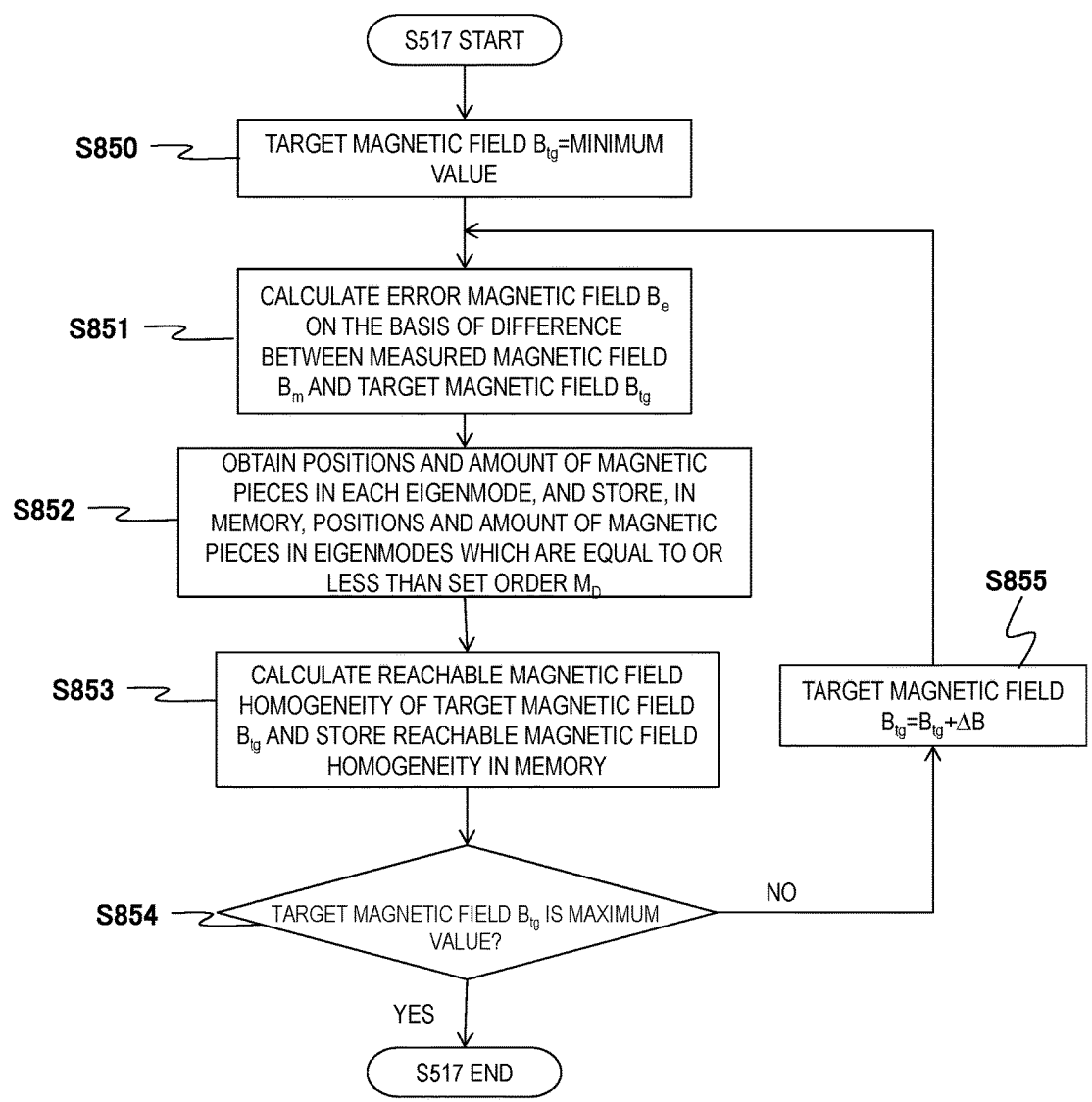
FIG. 8 is a flowchart illustrating details of S517 in FIG. 5.

A calculation method in S517 will be described in detail by using a flow in FIG. 8. First, in S851, the CPU 34 calculates an error magnetic field $B_e$ on the basis of the measured magnetic field $B_m$ calculated in S512 and the target magnetic field $B_{tg}$ received in S516.

$$B_e = B_m - B_{tg} \tag{1}$$

Here, $B_e$ is a matrix indicating an error magnetic field distribution, $B_m$ is a matrix indicating a distribution of the measured magnetic field, and $B_{tg}$ is a matrix indicating a homogeneous target magnetic field.

The error magnetic field $B_e$ may be expressed according to a linear equation in the following Equation (2).

$$B_e = AI \tag{2}$$

Here, $B_e$ is a matrix indicating an error magnetic field distribution, A is a response matrix of a magnetic field, and I is a matrix of a current potential indicating positions and an amount of magnetic pieces.

Here, if the response matrix A of a magnetic field is regular, an inverse matrix $A^{-1}$ is present, and the matrix I of a current potential indicating positions and an amount of magnetic pieces may be obtained according to the Equation (3).

$$I = A^{-1} B_e \tag{3}$$

The response matrix A is obtained in advance as follows by using magnetic moment of iron, a distance r between the depression 72 of the shim tray 71 of the MRI apparatus and an FOV (imaging field of view), and a vector r indicating an orientation. Magnetic moment m in point arrangement may be defined as a magnetic dipole of $m = (m_X, m_Y, m_Z)$ in any direction.

Generally, a magnetic field B (vector) formed by the magnetic moment m at a separated position of a position vector $R = (X, Y, Z)$ may be expressed by Equation (4). In Equations (4), (5) and (6), R indicates a position vector, and r indicates a distance.

$$B = (10^{-7}) \{ 3(m \cdot R) R / r^2 - m \} / r^3 \tag{4}$$

Here, if magnetic moment per unit volume is indicated by F, the magnetic moment m of the iron amount I is given as in Equation (5), and the response matrix A is expressed by Equation (6) in a case where magnetic moment (iron) is used to correct a magnetic field.

$$m = F \times I$$

In other words, $$B=\{(10^{-7})\{3(F\cdot R)R/r^2-F\}/r^3\}\times I \quad (5)$$

$$A=\{(10^{-7})\{3(F\cdot R)R/r^2-F\}/r^3\} \quad (6)$$

If a number j is added to the depression 72 of the shim tray 71, a magnetic field at a k-th measurement point is expressed by Equation (7) with respect to an iron amount $I_j$ (m$^3$) of each depression 72.

$$B_k=\Sigma A_{kj}I_j \quad (7)$$

However, the response matrix A expressed by Equation (6) is not regular, and thus an inverse matrix is not present, and thus singular value decomposition (SVD) is performed so that the response matrix A of a magnetic field is obtained according to Equation (8).

$$A=\Sigma u_i\cdot\lambda_i\cdot v_i^t \quad (8)$$

Here, i is the order of an eigenmode, $v_i$ is a matrix indicating an eigen distribution of a current potential in the order i, $u_i$ is a matrix indicating an eigen distribution of an error magnetic field in the order i, and $\lambda_i$ is a singular value.

The matrix I of a current potential indicating positions and an amount of magnetic pieces may be obtained according to Equation (9) on the basis of Equations (3) and (8).

$$I=\Sigma n_p^{1/2}P_iv_i/\lambda_i \quad (9)$$

Here, $Pi=u_i{}^tB_{ei}/n_p^{1/2}$, and $n_p$ is the number of measurement points of a magnetic field.

Figure 9:
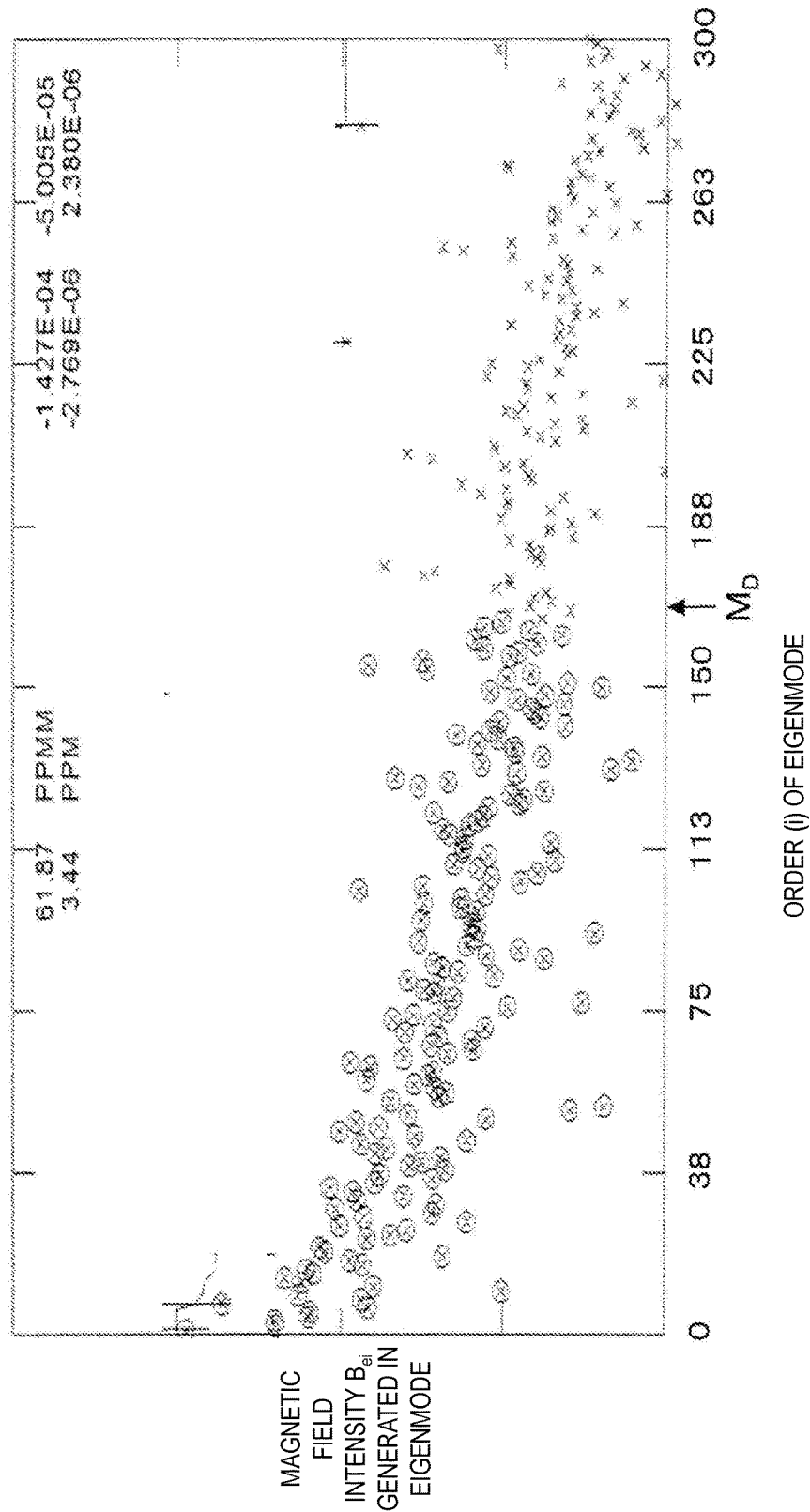
FIG. 9 is a graph illustrating a value of magnetic field intensity $B_{ei}$ generated for each eigenmode.

It can be seen from Equation (9) that the magnetic field intensity $B_{ei}$ generated in an eigenmode in the order i is expressed by $n_p^{1/2}P_iu_i$. The magnetic field intensities $B_{ei}$ in respective eigenmodes are distributed as illustrated in FIG. 9, and, as the order i becomes lower, the larger magnetic field intensity $B_{ei}$ is obtained. Therefore, a value of $n_p^{1/2}P_iu_i$ is added from the order i=1 to the order i=$M_D$ of the maximum value of an eigenmode received in S515, and is further added to the measured magnetic field $B_m$ as in the following Equation (6), and thus a predicted value $B_{Predicted}$ of an adjusted magnetic field distribution can be calculated.

$$B_{Predicted}=\Sigma_{i=1}{}^{MD}n_p^{1/2}P_iu_i+B_m \quad (10)$$

If a difference between the predicted value $B_{Predicted}$ of the adjusted magnetic field distribution obtained according to Equation (10) and the target magnetic field $B_{tg}$ is obtained, a matrix $B_{ep}$ indicating a distribution of non-homogeneous magnetic fields from the target magnetic field can be calculated.

$$B_{ep}=B_{Predicted}-B_{tg} \quad (11)$$

In S852, the CPU 34 performs calculation using Equations (8) and (9) so as to obtain positions and an amount of magnetic pieces in each eigenmode. Positions and an amount of magnetic pieces in eigenmodes which are equal to or less than the set maximum value $M_D$ are stored in the memory 35 in correlation with the target magnetic field $B_{tg}$. In a case where magnetic pieces are disposed in the depressions 72 at the same position in a plurality of eigenmodes, a total amount of magnetic pieces in the plurality of eigenmodes is calculated, and a total amount of magnetic pieces for each depression 72 is stored in the memory 35.

The calculated arrangement and an amount of magnetic pieces to be disposed in the depression 72 of the shim tray 71 are indicated by a matrix $I_J$. A matrix element $I_j$ of the matrix $I_J$ indicates an amount of magnetic pieces in the j-th depression 72. For example, if the number of shim trays 71 is 16, and the number of depressions 72 of the shim tray 71 is 20, the number of matrix elements $I_j$ of the matrix $I_J$ is 320 (where j=1 to 320).

In the above S852, in a case where the calculated amount of magnetic pieces exceeds the upper limit of an amount of magnetic pieces permitted to be disposed in the depression 72, received in S513, the calculated amount (the matrix element $I_j$ of the matrix $I_J$) of magnetic pieces is reduced to the upper limit of an amount of magnetic pieces permitted to be disposed according to Expression (12). Here, in Expression (12), $I_{max}$ indicates an upper limit of an amount of magnetic pieces permitted to be disposed in the depression 72.

$$0\le I_j\le I_{max} \quad (12)$$

($I_j=I_{max}$ if calculated $I_j>I_{max}$, and $I_j=I_j$ if calculated $I_j\le I_{max}$)

The matrix $I_J$ obtained after Expression (12) is applied indicates the amount and arrangement of magnetic pieces obtained by applying the upper limit for arrangement permission in the depression 72 to an amount of magnetic pieces for correcting an error magnetic field, calculated in S852. For example, as illustrated in FIG. 10, an amount of magnetic pieces is stored in the memory 35 in a table form of specifying a position of the depression 72 with a number of the depression 72.

A magnetic field generated according to the amount and arrangement of magnetic pieces indicated by the matrix $I_J$ is indicated by $AI_J$ on the basis of Equation (2), and thus a magnetic field $B_{Predicted}$ after the magnetic pieces are disposed and a matrix $B_{ep}$ indicating a non-homogeneous magnetic field distribution from the target magnetic field after the magnetic pieces are disposed may be obtained according to Equations (13) and (14) on the basis of Equations (10) and (11).

$$B_{Predicted}=AI_J+B_m \quad (13)$$

$$B_{ep}=B_{Predicted}-B_{tg} \quad (14)$$

The CPU 34 obtains the matrix $B_{ep}$ indicating a non-homogeneous magnetic field distribution by using the matrix $I_J$ indicating the amount and the distribution of magnetic pieces, obtained in S852, and Equations (13) and (14). Here, in Equation (13), Equation (8) is used as the response matrix A.

In S853, the CPU 34 calculates reachable magnetic field homogeneity (reach predicted magnetic field homogeneity) on the basis of matrix elements of the matrix $B_{ep}$ indicating the non-homogeneous magnetic field. For example, a relative value of a difference (a PkPk value: a peak-to-peak value) between the maximum value and the minimum value of an error magnetic field indicated by the matrix $B_{ep}$ for average magnetic field intensity is calculated according to Equation (15), and thus the non-homogeneous magnetic field is obtained. The calculated magnetic field homogeneity is stored in the memory 35 in correlation with the target magnetic field $B_{tg}$.

Magnetic field homogeneity (*PkPk* value)={(maximum value of matrix elements of matrix $B_{ep}$)−(minimum value of matrix elements of matrix $B_{ep}$)}/(average magnetic field intensity)×10$^{-6}$ [ppm] (15)

The calculations in S851 to S853 are repeatedly performed by changing the target magnetic field $B_{tg}$ from the minimum value ($B_{tgc}-\Delta B\cdot n/2$) of the set magnetic field range to the maximum value ($B_{tgc}+\Delta B\cdot n/2$) by $\Delta B$. Consequently, reachable magnetic field homogeneity can be calculated for each of n target magnetic fields with the pitch width ΔB within the set magnetic field range.

FIGS. 11(a) to 11(c) and FIGS. 12(a) to 12(c) illustrate examples of computation results in the forms of a table and a graph. FIG. 11(a) as an example of a calculation result will be described. In the example illustrated in FIG. 11(a), if ΔB=5×10$^{-4}$ teslas, and n=6, reachable magnetic field homogeneities are calculated for six target magnetic fields $B_{tg}$ within a range from 1.498848 teslas or more to 1.501348 teslas or less. The results illustrated in FIG. 11(a) are shown in FIG. 12(a) in the form of a graph. FIG. 11(a) and FIG. 12(a) illustrate a total capacity of magnetic pieces to be disposed with respect to magnetic pieces having positive magnetic moment and magnetic pieces having negative magnetic moment.

Here, with reference to FIGS. 11(a) and 12(a), a description will be hereinafter made of an embodiment in a case where necessary magnetic field homogeneity is set to be 10 ppm or less, and a total amount of positive magnetic moment is set to be 1.5×10$^{-3}$ m$^3$ (about 12 kg in a case where a magnetic piece is iron or an electromagnetic steel sheet) or less, and a total amount (lower limit value) of negative magnetic moment is set to be 0, with respect to a total capacity of magnetic pieces which can be disposed.

As can be seen from FIG. 12(a), the reachable magnetic field homogeneity is also changed according to a change of the target magnetic field $B_{tg}$. The CPU 34 determines whether or not an amount and a total capacity of magnetic pieces for the depression 72 at each position of the shim tray 71 are equal to or less than a predetermined upper limit value, and there is the target magnetic field $B_{tg}$ in which the reachable magnetic field homogeneity is equal to or less than a predetermined value on the basis of the calculation result of the reachable magnetic field homogeneity calculated in S853 (S518), and selects the target magnetic field $B_{tg}$ if there is the target magnetic field satisfying the conditions (S519).

For example, in the examples illustrated in FIG. 11(a) and FIG. 12(a), there is the target magnetic field $B_{tg}$ in which the reachable magnetic field homogeneity is 9.3 ppm as the minimum value, and, regarding a total amount of magnetic pieces, a positive magnetic moment total amount satisfies the restriction condition (1.5×10$^{-3}$ m$^3$ or less), but a negative total amount is −5.6×10$^{-4}$ m$^3$ and thus does not satisfy the restriction condition. Therefore, the target magnetic field $B_{tg}$ (1.499848 teslas, and the magnetic field homogeneity of 9.9 ppm) which satisfies the restriction condition, and satisfies the necessary magnetic field homogeneity 10 ppm or less is selected.

In the example illustrated in FIG. 12(a), regarding magnetic pieces, since only magnetic pieces having positive magnetic moment are necessary, and an amount of magnetic pieces having negative magnetic moment is 0, it is not necessary to use a permanent magnet piece, and this is preferable.

If there is no target magnetic field $B_{tg}$ satisfying the conditions in S518, the flow returns to S513, the operator sets other conditions in S513 to S517, and performs computation again.

The CPU 34 displays arrangement and an amount of magnetic pieces for each depression 72 of the shim tray 71, stored in S852 for the target magnetic field $B_{tg}$ (=1.499848 teslas) selected in S519, on the display device as magnetic pieces to be disposed in the shim tray 71 (S520). For example, as illustrated in FIG. 10, a table showing an amount of magnetic pieces for each depression 72 is displayed on the display device.

The operator checks an amount and a position (a number of the depression 72 of the shim tray 71) of magnetic pieces displayed on the display device, and inserts magnetic pieces of the amount displayed into each depression 72 of the shim tray 71. Consequently, adjustment of the static magnetic field homogeneity is completed.

In a case where the static magnetic field generation device is a static magnetic field generation device of an MRI apparatus, the CPU 34 calculates a frequency of a high frequency magnetic field for exciting nuclear magnetism of an object disposed under the target magnetic field $B_{tg}$ (=1.499848 teslas) selected in S519, and displays the calculated frequency on the display device (S521). The operator sets the displayed frequency of a high frequency magnetic field so that a high frequency magnetic field with the frequency is applied from a high frequency magnetic field generation unit of the MRI apparatus. Consequently, the MRI apparatus can image the object with high accuracy according to the adjusted target magnetic field $B_{tg}$.

In the present embodiment, low-order modes from the order i=1 to the set order $M_D$ are used as eigenmodes, and thus a singular value λi having a great value in the low-order mode can be used so that a large correction magnetic field can be generated with a small magnetic body amount. Therefore, it is possible to reduce a magnetic body amount and thus to efficiently adjust a magnetic field.

According to the present embodiment, the target magnetic field $B_{tg}$ is changed, and thus it is possible to achieve necessary magnetic field homogeneity by taking into consideration an upper limit value in an amount of magnetic pieces which can be disposed in the depression 72 of the shim tray 71.

As illustrated in FIG. 7, the screen for inputting set conditions from an operator may be provided with an input column 67 for receiving a size of a necessary homogeneous magnetic field, or columns 69a and 69b in which the CPU 34 computes and displays a center magnetic field and homogeneity of a measured magnetic field acquired in S512.

An operator may select a target magnetic field (optimal value) on the basis of changes of the respective magnetic field homogeneities calculated while changing a target magnetic field within a predetermined magnetic field range.

<<Second Embodiment>>

A description will be made of a magnetic field homogeneity adjustment method according to a second embodiment. In the second embodiment, even in a case where a distribution of measured magnetic fields is large (for example, 100 to 1000 ppm) with respect to necessary magnetic field homogeneity (for example, 10 ppm or less), arrangement and an amount of magnetic pieces for achieving the magnetic field homogeneity are efficiently obtained by repeating computation of reachable magnetic field homogeneity while changing the width ΔB with which a target magnetic field is changed. This will be described with reference to a flow illustrated in FIG. 13.

First, the CPU 34 executes S512 to S519 in FIG. 5 in the first embodiment so as to select the target magnetic field $B_{tg}$ satisfying the conditions. The flow proceeds to S5121, a second magnetic field range narrower than the magnetic field range which is set in S516, including the target magnetic field $B_{tg}$ selected in S519, is set. A pitch width ΔB2 smaller than ΔB set in S516 is set.

For example, three kinds such as 5×10$^{-4}$ teslas, 2×10$^{-4}$ teslas, and 1×10$^{-5}$ teslas are prepared as the pitch width ΔB2, and, among the three kinds of pitch widths, a pitch width which is equal to or less than ΔB used in the previous S518 and is close to ΔB may be selected. For example, in a case where ΔB in S516 is $5\times10^{-4}$ teslas, $2\times10^{-4}$ teslas is selected as ΔB2. The target magnetic field $B_{tg}$ selected in S519 is set as a center value $B_{tgc}$ of a target magnetic field, and the second magnetic field range may be set to n (where n is an integer) times the pitch width ΔB2.

The flow proceeds to S1322, and reachable magnetic field homogeneity is calculated again by changing the target magnetic field $B_{tg}$ by the pitch width ΔB2 within the second magnetic field range. In S1323, the target magnetic field $B_{tg}$ in which an amount of magnetic pieces for each depression 72 of the shim tray 71 is equal to or less than a predetermined upper limit value and the magnetic field homogeneity is the minimum is selected on the basis of the calculation result in S1322. An example of the calculation result in S1322 is shown in the form of a table in FIG. 11(b).

In the example illustrated in FIG. 11(b), if the center $B_{tgc}$ of the target magnetic field $B_{tg}$ is 1.499848 teslas selected in S519, ΔB2=$2\times10^{-4}$ teslas, and n=6, reachable magnetic field homogeneities are calculated for six target magnetic fields $B_{tg}$ within a range from 1.499248 teslas or more to 1.500248 teslas or less. The target magnetic field $B_{tg}$ (=1.500048 teslas) is selected in which an amount of magnetic pieces for each depression 72 of the shim tray 71 is equal to or less than a predetermined upper limit value and the magnetic field homogeneity is the minimum. The magnetic field homogeneity at that time is 8.7 ppm.

Next, the flow proceeds to S1324, and it is determined whether or not the set pitch width ΔB2 is the predefined minimum value. For example, in a case where three kinds such as $5\times10^{-4}$ teslas, $2\times10^{-4}$ teslas, and $1\times10^{-5}$ teslas are prepared as the pitch width ΔB2, ΔB2 is not the minimum value, $1\times10^{-5}$ teslas, yet, and thus the flow returns to S5121.

In S5121, a second magnetic field range narrower than the previous magnetic field range, including the target magnetic field $B_{tg}$ selected in S1323, is set. The pitch width ΔB2 is also set to a value smaller than the previous width. For example, $1\times10^{-5}$ teslas is set as the pitch width ΔB2, the target magnetic field $B_{tg}$ selected in S1323 is set as a center value $B_{tgc}$ of a target magnetic field, and the second magnetic field range may be set to n (where n is an integer) times the pitch width ΔB2.

The flow proceeds to S1322, and reachable magnetic field homogeneity is calculated again by changing the target magnetic field $B_{tg}$ by the pitch width ΔB2 within the second magnetic field range. An example of the calculation result in S1322 is shown in the form of a table in FIG. 11(c).

In the example illustrated in FIG. 11(c), if the center $B_{tgc}$ of the target magnetic field $B_{tg}$ is 1.500048 teslas selected in S1323, ΔB2=$1\times10^{-5}$ teslas, and n=6, reachable magnetic field homogeneities are calculated for six target magnetic fields $B_{tg}$ within a range from 1. 500018 teslas or more to 1.500068 teslas or less. The target magnetic field $B_{tg}$ is 1.500058 teslas in which an amount of magnetic pieces for each depression 72 of the shim tray 71 is equal to or less than a predetermined upper limit value, an amount of negative magnetic pieces is zero, and the magnetic field homogeneity is the minimum as 8.6 ppm.

FIG. 11(c) is shown in the form of a graph in FIG. 12(c). As illustrated in FIG. 12(c), necessary magnetic field homogeneity is achieved at all of six target magnetic fields from 1.500018 teslas to 1.500068 teslas, the minimum magnetic field homogeneity is 8.5 ppm at the target magnetic field $B_{tg}$ of 1.500068 teslas, but a negative amount of magnetic pieces is $-4.9\times10^{-10}$, which does not satisfy the restriction condition regarding a magnetic piece arrangement amount, and thus cannot be selected. Therefore, 1.500058 teslas corresponding to magnetic field homogeneity in which an amount of magnetic pieces is the minimum within the restriction condition is selected as a target magnetic field.

Here, a negative lower limit value is zero as the restriction condition, but the negative amount of magnetic pieces of $-4.9\times10^{-10}$ may be a negligible magnitude depending on a unit amount of magnetic pieces, and favorable magnetic field homogeneity may be achieved. As mentioned above, a restriction condition may be set by taking into consideration a unit amount of magnetic pieces and an existing magnetic piece arrangement amount.

The flow proceeds to S520, and, in the same manner as in the first embodiment, arrangement of magnetic bodies and an amount thereof corresponding to the target magnetic field $B_{tg}$ selected in S1323 are displayed on the display device as magnetic pieces to be disposed in the depression 72 of the shim tray 71. For example, the table of the depressions 72 of the shim tray 71 and magnetic body amounts in FIG. 10 is displayed. The flow further proceeds to S521, and a frequency of a high frequency magnetic field corresponding to the selected target magnetic field $B_{tg}$ is calculated and displayed.

In the second embodiment, even in a case where a homogeneity of measured magnetic fields is large (for example, 100 to 1000 ppm) with respect to necessary magnetic field homogeneity (for example, 10 ppm or less), a range of a target magnetic field and the pitch width ΔB are gradually reduced, and reachable magnetic field homogeneity is repeatedly calculated. Thus, it is possible to efficiently obtain arrangement and an amount of magnetic bodies for achieving necessary magnetic field homogeneity.

In the second embodiment, configurations and operations other than those described above are the same as those in the first embodiment, and thus description thereof will be omitted.

<<Third Embodiment>>

Figure 14:
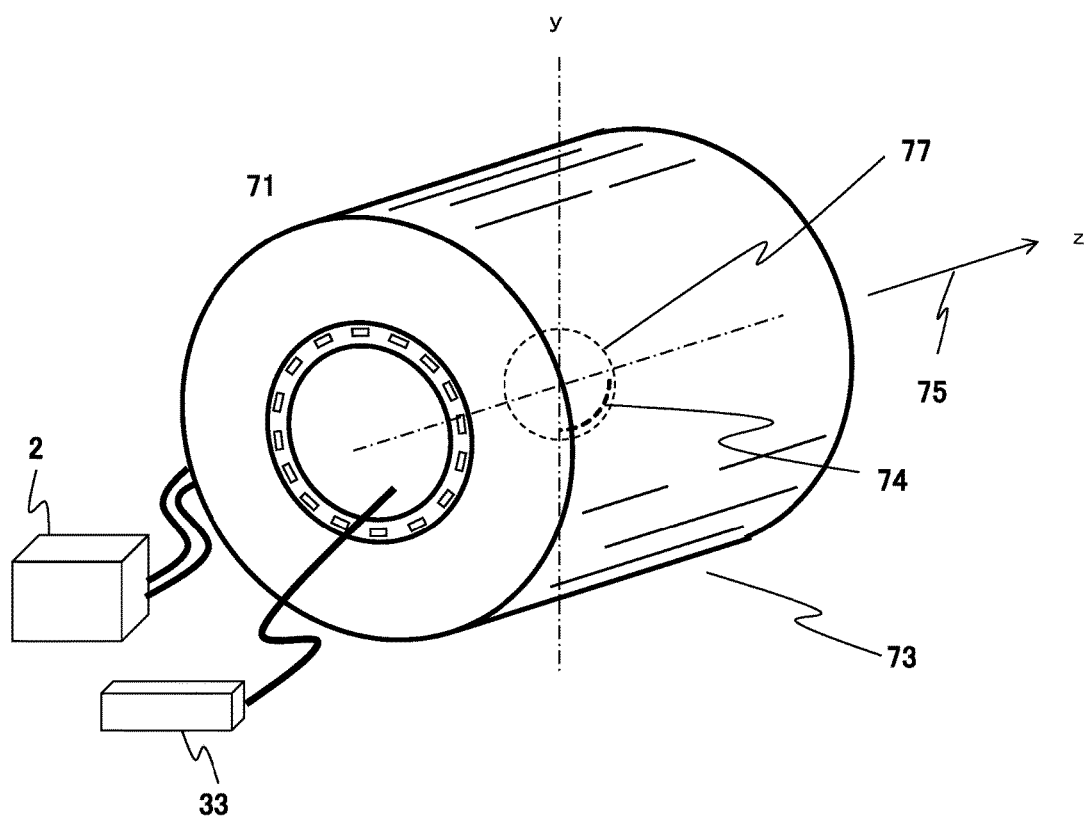
FIG. 14 is a perspective view illustrating a static magnetic field generation device in which a magnetic field homogeneity adjustment device 33 according to a third embodiment is disposed.

In a third embodiment, a description will be made of a case where magnetic field measurement or excitation of a superconducting magnet of a static magnetic field generation device is automatically performed. In the present embodiment, as illustrated in FIGS. 4 and 14, the homogeneous magnetic field adjustment device 33 is connected to the measurement unit 74 disposed in the homogeneous magnetic field space 77 of the static magnetic field generation device, and the excitation power source 2 of the superconducting coil 4a built into the static magnetic field generation device 73.

As illustrated in a flow in FIG. 15, first, the CPU 34 of the homogeneous magnetic field adjustment device 33 controls the excitation power source 2 so as to supply a predetermined superconducting current to the superconducting coil 4a and to excite the superconducting coil (S511). In S512, the CPU 34 controls an operation of the measurement device 74 so as to rotate the measurement device 74 in the homogeneous magnetic field space 77, and measures a magnetic field. Conditions are set in S513 to S516.

In the present embodiment, in S513 and S514, positions and an upper limit value of an amount of magnetic pieces, and necessary magnetic field homogeneity are received from the operator in the same manner as in the first embodiment, but a predefined value is used as the maximum value $M_D$ of an eigenmode in S515.

In S516, a range of the target magnetic field $B_{tg}$ is not received from the operator, a value between the maximum value and the minimum value of the magnetic field distributions measured in S512 is calculated by using a predetermined numerical expression (for example, an average value) so as to be set as the center value $B_{tgc}$ of the target magnetic field $B_{tg}$, and $(B_{tgc}-\Delta B \cdot n/2)$ to $(B_{tgc}+\Delta B \cdot n/2)$ is set as the magnetic field range by using the predefined $\Delta B$ and n.

S517 to S521 are executed in the same manner as in the first embodiment.

In S1522, it is determined whether or not the total amount of magnetic pieces displayed in S520 is equal to or less than a total amount in which the shim tray 71 is extracted from the static magnetic field generation device 73 in a state in which the superconducting coil 4a is excited, magnetic pieces are disposed in the depressions 72, and the shim tray 71 can be inserted again.

In other words, if a total amount of magnetic pieces is small, attraction force given by a static magnetic field is small, and thus the shim tray can be disposed in the excitation state. However, in a case where an amount of magnetic pieces is large, great attraction force acts, and thus the shim tray cannot be disposed in the excitation state. Thus, the flow proceeds to S1523, and the superconducting magnet 4a is temporarily demagnetized. Since demagnetization and then re-excitation require not only time and but also cost of a refrigerant, in S1522, whether or not the shim tray can be disposed in an excitation state is determined by comparing a total amount of magnetic pieces obtained in advance through computation with the total amount of magnetic pieces displayed in S520. If demagnetization is not necessary, the flow proceeds to S1524 without demagnetization. If demagnetization is necessary, the flow proceeds to S1523, and the CPU 34 controls the excitation power source 2 causes an excitation current to be zero or to be reduced to a predetermined value, and then proceeds to S1524.

In S1524, the CPU performs display for prompting the operator to dispose magnetic pieces in the depressions 72 of the plurality of shim trays 71 as displayed in S520.

If the operator disposes the magnetic pieces, an operation of the measurement unit 74 is controlled in S1525, and a magnetic field is measured again. In a case where excitation is performed in S1523, an excitation current is supplied to the superconducting coil 4a from the excitation power source 2 before measurement, and thus the superconducting coil is excited again.

In S1526, the homogeneity of the magnetic field measured in S1525 is calculated, and it is determined whether or not the homogeneity is equal to or less than the necessary magnetic field homogeneity received in S514. If the measured magnetic field homogeneity is equal to or less than the necessary magnetic field homogeneity, adjustment of the magnetic field homogeneity is finished. If the measured magnetic field homogeneity is more than the necessary magnetic field homogeneity, the flow returns to S513, and S513 and the subsequent steps are repeatedly performed.

In this case, when a restriction condition of a magnetic body amount is set in S513, magnetic pieces are already disposed in S1524, thus this is permitted, and an upper limit value is set. For example, in a case where magnetic pieces of $2.0 \times 10^{-6}$ m$^3$ can be disposed in each depression 72, if an upper limit value of an amount of magnetic pieces is set to $1.5 \times 10^{-6}$ m$^3$ for the first time, an upper limit value is set to a value smaller than $0.5 \times 10^{-6}$ m$^3$ in the second S513.

In the present embodiment, the CPU 34 can automatically perform excitation of the superconducting coil 4a and demagnetization thereof as necessary, and measurement of a magnetic field without troubling hands of an operator, and thus it is possible to reduce a burden on the operator. Since necessity and unnecessity of demagnetization are automatically determined, the number of times of demagnetization can also be reduced to the minimum required.

In a case where demagnetization is performed in S1523, and then re-excitation is performed in S1524, magnetic field intensity after the re-excitation may be different from original magnetic field intensity due to an error of an excitation current value which depends on the accuracy of the excitation power source 2. Thus, the target magnetic field $B_{tg}$ used to compute arrangement and an amount of magnetic pieces after the re-excitation is required to be changed according to an excitation current value (that is, magnetic field intensity after the re-excitation), but, in the present embodiment, in S516, a target magnetic field is set through computation on the basis of a distribution of a magnetic field measured in S512 or 25, and thus arrangement of necessary magnetic field homogeneity can be obtained according to an error of an excitation current value after the re-excitation.

In the third embodiment, configurations other than the above-described configurations are the same as those in the first embodiment, and thus description thereof will be omitted. S511 and S1522 to S1526 in the third embodiment may be performed before S512 and after S521 of the flow in FIG. 13 in the second embodiment, in addition to the first embodiment.

In the first to third embodiments, the maximum value $M_D$ of eigenmodes used for computation is received in S515, and positions and an amount of magnetic pieces, and magnetic field homogeneity are calculated by changing only the target magnetic field $B_{tg}$ in S517, but, the computation in S517 may be performed by changing both of the target magnetic field $B_{tg}$ and the maximum value $M_D$ of eigenmodes. In this case, a combination between the target magnetic field $B_{tg}$ which can further reduce magnetic field homogeneity and the optimal maximum value $M_D$ of eigenmodes, and positions and an amount of magnetic pieces at that time can be obtained.

In the first to third embodiments, an eigenmode is selected within a predetermined low-order range (a range of the order of 1 to the maximum value $M_D$), but the present embodiment is not limited thereto, and a high-order eigenmode range may be selected, and eigenmodes in a plurality of any orders may be selected at random.

REFERENCE SIGNS LIST

2 EXCITATION POWER SOURCE, 4a SUPERCONDUCTING COIL, 33 MAGNETIC FIELD HOMOGENEITY ADJUSTMENT DEVICE, 34 CPU, 35 MEMORY, 71 SHIM TRAY, 72 DEPRESSION, 73 STATIC MAGNETIC FIELD GENERATION DEVICE, 74 MEASUREMENT UNIT, 77 HOMOGENEOUS MAGNETIC FIELD SPACE

The invention claimed is:

1. A magnetic field homogeneity adjustment method using singular value decomposition for a static magnetic field generation device including a shim tray for holding magnetic pieces for adjusting homogeneity of a generated static magnetic field at a plurality of predetermined positions, the method comprising:

measuring a distribution of a static magnetic field generated by the static magnetic field generation device so as to calculate an error magnetic field between the distribution of the static magnetic field and a target magnetic field;

calculating, in a case where the magnetic pieces are disposed at one or more positions amongst the plurality of positions in the shim tray, reachable magnetic field homogeneities at the one or more respective positions, while changing the target magnetic field within a predetermined magnetic field range; and selecting the target magnetic field in which, at each position amongst the plurality of positions, an amount of magnetic pieces at the position is equal to or less than a predetermined upper limit value, and the reachable magnetic field homogeneity at the position is equal to or less than a predetermined value, and disposing the magnetic pieces of the amount corresponding to the target magnetic field in the shim tray.

2. The magnetic field homogeneity adjustment method according to claim 1, wherein a second magnetic field range which includes the selected target magnetic field and is narrower than the predetermined magnetic field range is set, and for each position amongst the plurality of positions, the reachable magnetic field homogeneity at the position is calculated again by changing the target magnetic field within the second magnetic field range, the target magnetic field is selected in which an amount of magnetic pieces at the position is equal to or less than a predetermined upper limit value, and the reachable magnetic field homogeneity is the minimum, and the magnetic pieces of the amount corresponding to the selected target magnetic field are disposed in the shim tray.

3. The magnetic field homogeneity adjustment method according to claim 1, wherein arrangement of the magnetic pieces and an amount thereof are calculated by using a plurality of eigenmodes which are calculated according to the singular value decomposition.

4. The magnetic field homogeneity adjustment method according to claim 3, wherein, among the plurality of eigenmodes, only eigenmodes in a plurality of predetermined orders are selectively used, and arrangement of the magnetic pieces and an amount thereof are calculated.

5. The magnetic field homogeneity adjustment method according to claim 1, wherein, in a case where the static magnetic field generation device is a static magnetic field generation device of a magnetic resonance imaging apparatus, a frequency of a high frequency magnetic field corresponding to the obtained target magnetic field is calculated, and is set in a high frequency magnetic field generated unit of the magnetic resonance imaging apparatus.

6. The magnetic field homogeneity adjustment method according to claim 1, wherein a center value of the target magnetic field is set on the basis of the measured distribution of the static magnetic field, and the predetermined magnetic field range is set centering on the center value of the target magnetic field.

7. The magnetic field homogeneity adjustment method according to claim 1, wherein the target magnetic field is selected on the basis of changes of the respective magnetic field homogeneities calculated while changing the target magnetic field within a predetermined magnetic field range.

8. A magnetic field homogeneity adjustment program of executable instruction embodied in a non-transitory medium and causing a computer to perform a method for adjusting magnetic field homogeneity for a static magnetic field generation device including a shim tray for holding magnetic pieces for adjusting homogeneity of a generated static magnetic field at a plurality of predetermined positions, the method comprising:

a first step of acquiring a measurement result of a static magnetic field generated by the static magnetic field generation device so as to calculate an error magnetic field between the static magnetic field and a target magnetic field;

a second step of calculating, in a case where the magnetic pieces are disposed at one or more positions amongst the plurality of positions in the shim tray, reachable magnetic field homogeneities at the one or more respective positions, while changing the target magnetic field within a predetermined magnetic field range;

a third step of selecting the target magnetic field in which, at each position amongst the plurality of positions, an amount of magnetic pieces at the position is equal to or less than a predetermined upper limit value, and the reachable magnetic field homogeneity at the position is equal to or less than a predetermined value, on the basis of a calculation result of the reachable magnetic field homogeneity calculated in the second step; and a fourth step of displaying arrangement of the magnetic pieces and an amount thereof corresponding to the target magnetic field selected in the third step, on a display device.

9. The magnetic field homogeneity adjustment program according to claim 8, wherein the method performed by the computer executing the program of executable instructions further comprises:

a fifth step of setting a second magnetic field range which includes the target magnetic field selected in the third step and is narrower than the predetermined magnetic field range;

a sixth step of calculating again the reachable magnetic field homogeneity by changing the target magnetic field within the second magnetic field range; and a seventh step of selecting the target magnetic field in which, at each position amongst the plurality of positions in the tray, an amount of magnetic pieces at the position is equal to or less than a predetermined upper limit value, and the reachable magnetic field homogeneity is the minimum, on the basis of a calculation result in the sixth step, wherein, in the fourth step, arrangement of the magnetic pieces and an amount thereof corresponding to the target magnetic field selected in the seventh step are displayed on the display device.

10. The magnetic field homogeneity adjustment program according to claim 8, wherein, in the second step, arrangement of the magnetic pieces and an amount thereof are calculated by using a plurality of eigenmodes which are calculated according to the singular value decomposition.

11. The magnetic field homogeneity adjustment program according to claim 10, wherein, in the second step, a plurality of orders used to calculate arrangement of the magnetic pieces and an amount thereof are received from an operator.

12. The magnetic field homogeneity adjustment program according to claim 10, wherein, in the second step, the reachable magnetic field homogeneity is calculated by changing both of the target magnetic field and the order of the eigenmode.

13. The magnetic field homogeneity adjustment program according to claim 8, further causing the computer to execute:

an eighth step of calculating a frequency of a high frequency magnetic field corresponding to the target magnetic field selected in the third step in a case where the static magnetic field generation device is a static magnetic field generation device of a magnetic resonance imaging apparatus; and a ninth step of displaying the frequency of a high frequency magnetic field calculated in the eighth step on the display device as a frequency to be set in a high frequency magnetic field generated unit of the magnetic resonance imaging apparatus.

14. The magnetic field homogeneity adjustment program according to claim 8,
wherein, in the second step, a center value of the target magnetic field is set within a distribution width of the static magnetic field on the basis of the distribution of the static magnetic field calculated in the first step, and the predetermined magnetic field range is set centering on the center value of the target magnetic field.

15. A magnetic field homogeneity adjustment device adjusting magnetic field homogeneity for a static magnetic field generation device including a shim tray for holding magnetic pieces for adjusting the homogeneity of a generated static magnetic field at a plurality of predetermined positions, the magnetic field homogeneity adjustment device comprising:

a reception unit that receives a measurement result of a static magnetic field generated by the static magnetic field generation device, an upper limit value of an amount of magnetic pieces at the plurality of positions, and a range of a target magnetic field; and a calculation unit that calculates arrangement and an amount of the magnetic pieces to be disposed in the shim tray by using the conditions received by the reception unit, wherein the calculation unit calculates an error magnetic field between the static magnetic field and a target magnetic field, calculates, in a case where the magnetic pieces are disposed at one or more positions amongst the plurality of positions in the shim tray, reachable magnetic field homogeneities at the one or more respective positions, while changing the target magnetic field within the range of the target magnetic field received by the reception unit, selects the target magnetic field in which, at each position amongst the plurality of positions, an amount of magnetic pieces at the position is equal to or less than the received upper limit value, and the reachable magnetic field homogeneity at the position is equal to or less than a predetermined value, on the basis of a calculation result of the calculated reachable magnetic field homogeneity, and displays arrangement of the magnetic pieces and an amount thereof corresponding to the selected target magnetic field on a display device.

\* \* \* \* \*